US012667254B2

(12) United States Patent
Rege

(10) Patent No.: US 12,667,254 B2
(45) Date of Patent: Jun. 30, 2026

(54) ILLUMINATION OF AN EYE FUNDUS USING NON-SCANNING COHERENT LIGHT

(71) Applicant: VASOPTIC MEDICAL INC., Columbia, MD (US)

(72) Inventor: Abhishek Rege, Columbia, MD (US)

(73) Assignee: Vasoptic Medical Inc., Columbia, MD (US)

( * ) Notice: Subject to any disclaimer, the term of this patent is extended or adjusted under 35 U.S.C. 154(b) by 759 days.

(21) Appl. No.: 17/941,348

(22) Filed: Sep. 9, 2022

(65) Prior Publication Data

US 2023/0064792 A1 Mar. 2, 2023

Related U.S. Application Data

(63) Continuation of application No. PCT/US2021/021695, filed on Mar. 10, 2021.

(60) Provisional application No. 62/989,224, filed on Mar. 13, 2020.

(51) Int. Cl.
*A61B 3/12* (2006.01)
*A61B 3/00* (2006.01)
*A61B 3/15* (2006.01)

(52) U.S. Cl.
CPC .............. *A61B 3/12* (2013.01); *A61B 3/0025* (2013.01); *A61B 3/152* (2013.01); *A61B 3/156* (2013.01)

(58) Field of Classification Search
CPC ........... A61B 3/10; A61B 3/12; A61B 3/0025; A61B 3/152; A61B 3/156
See application file for complete search history.

(56) References Cited

U.S. PATENT DOCUMENTS

| | | | |
|---|---|---|---|
| 2007/0291226 A1 | 12/2007 | Fujii | |
| 2008/0123052 A1* | 5/2008 | Su | A61B 3/12 351/221 |
| 2011/0116040 A1 | 5/2011 | Biernat et al. | |
| 2014/0247427 A1 | 9/2014 | Ferguson et al. | |

(Continued)

FOREIGN PATENT DOCUMENTS

| | | |
|---|---|---|
| CN | 103300816 A | 9/2013 |
| DE | 7234749 U | 1/1973 |

(Continued)

OTHER PUBLICATIONS

International Search Report and Written Opinion mailed on Aug. 16, 2021 for corresponding International Patent Application No. PCT/US2021/021695, filed Mar. 10, 2021.

(Continued)

*Primary Examiner* — Bumsuk Won
*Assistant Examiner* — Alex Park Rickel
(74) *Attorney, Agent, or Firm* — Pierce Atwood LLP

(57) ABSTRACT

Imaging various regions of the eye is important for both clinical diagnostic and treatment purposes as well as for scientific research. Diagnosis of a number of clinical conditions relies on imaging of the various tissues of the eye. The subject technology describes a method and apparatus for imaging the eye using off-center illumination in a manner that avoids light striking the anterior surfaces of the eye at or near a center of the optical axis, thereby reducing reflections traveling back along an imaging light path, while also providing substantially uniform illumination of a region of interest of the fundus.

16 Claims, 15 Drawing Sheets

(56) References Cited

U.S. PATENT DOCUMENTS

2019/0008380 A1 * 1/2019 Hayashi ................. A61B 3/103
2019/0046031 A1 * 2/2019 Kramer ................... A61B 3/14

FOREIGN PATENT DOCUMENTS

DE           4301574  A1      7/1994
JP           H1128191  A  *   2/1999
WO      WO-2012134272  A1  *  10/2012    ............... A61B 3/14

OTHER PUBLICATIONS

European Office Action mailed on Jul. 29, 2025 for corresponding
European Patent Application No. 21715417.8, 11 pages.

* cited by examiner

Profile of the illuminating beam at the cornea as (A) 2-dimensional plot, and (B) a surface plot Profile of the illuminating beam at the retina

1300

ILLUMINATION OF AN EYE FUNDUS USING NON-SCANNING COHERENT LIGHT

CROSS-REFERENCE TO RELATED APPLICATIONS

This application claims priority to P.C.T. Application No. PCT/US2021/021695, filed Mar. 10, 2021, entitled "ILLU-MINATION OF AN EYE FUNDUS USING NON-SCAN-NING COHERENT LIGHT", which claims priority to U.S. Provisional Application No. 62/989,224, filed Mar. 13, 2020, entitled "ILLUMINATION OF AN EYE FUNDUS USING NON-SCANNING COHERENT LIGHT." The entire contents of each are incorporated herein by reference for all purposes.

GOVERNMENT LICENSE RIGHTS

This invention utilized government support under grant 2R44AG048758 awarded by the National Institute on Aging (of the National Institutes of Health). The government has certain rights in the invention.

FIELD

The subject technology relates to imaging regions of tissue. In particular, the subject technology relates to illu-minating and acquiring images of a fundus of an eye.

BACKGROUND

Imaging the internal regions of the eye is important for both clinical diagnostic and treatment purposes as well as for scientific research. Diagnosis of a number of clinical con-ditions (e.g., diabetic retinopathy (DR), hypertensive ret-inopathy (RR), age related macular degeneration (AMD), retinopathy of prematurity (ROP), retinal detachment, glau-coma, cataract, and various types of neovascularization pathologies in the choroid (CNV), cornea and retina) relies on imaging appropriately the retina, choroid, the cornea, the sclera, or the eye lens, including imaging specific aspects of each of these tissues (e.g., blood, blood vessels, exudates, and other anatomical and physiological features). A number of these pathophysiologies are gradual-that is, these disor-ders develop over time-making a strong case for timely diagnosis and management. For example, unmanaged dia-betes and DR leads to proliferation of blood vessels in the retina, blood leakage into the eye and eventually, loss of vision. Thus, not only does retinal imaging have a role in detecting the evidence of a pathophysiology, but also in diagnosing its severity. Early diagnosis through routine monitoring is important in disease management and, hence, eye screening is becoming an increasingly important aspect in primary care.

In addition to these ophthalmic diseases, imaging of the blood vessels of ophthalmic tissue can be used to detect non-ophthalmic diseases or conditions. These non-ophthal-mic disease or conditions can be organ-specific or systemic. For example, reports in literature have also indicated that early signs of brain disorders are also manifested in the retina. Thus, imaging the retina can be used for early diagnosis or risk assessment of conditions like stroke and other types of brain lesions. Similarly, systemic disease (e.g., heart disease or diabetes) can be diagnosed and monitored based on an evaluation of the retinal blood vessels.

DETAILED DESCRIPTION

Figure 1:
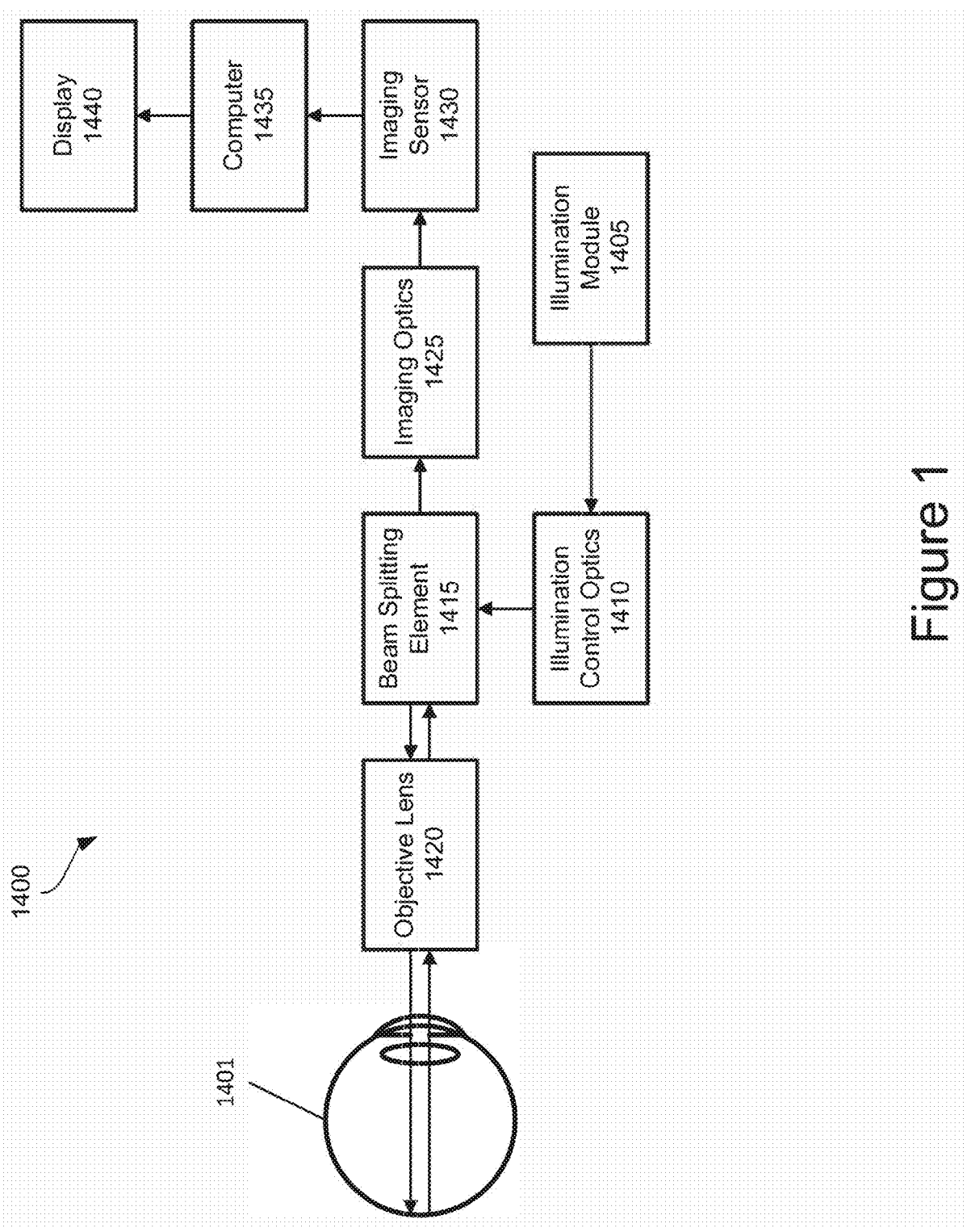
FIG. 1 is a schematic of components of an OID system configured for off-axis illumination of an eye.

The subject technology describes a method and apparatus for imaging of the back of the eye (i.e., the retina and/or the choroid) using illumination from at least one non-scanning coherent light source. The apparatus, embodied as an oph-thalmic imaging device (called "OID" hereafter), may use coherent illumination that is generated by any type of laser source, and any type of camera to acquire image data. The OID includes a method and apparatus for illuminating the back of the eye after travelling through the pupil of the eye while reducing the amount of illuminating light that reaches the camera after bouncing back from the anterior structures of the eye.

Additional illumination modalities may be used to enable additional imaging modalities. For example, imaging may be carried out under coherent and incoherent illumination, the timing of which can be controlled for the desired imaging technique or two types. The coherent illumination may comprise light from different sources that are different in at least one property such as wavelength. Coherent illumination means the degree of coherence of the emitted optical beam is high (e.g., green, red, blue, or near infrared laser) and includes, among other things, various types of lasers including diode lasers, gas lasers, and vertical cavity surface emitting lasers (VCSEL). Incoherent illumination means the degree of coherence of the emitted optical beam is low (e.g., white or spectrally filtered light from a light emitting diode (LED) or a halogen lamp). Use of multiple illumination modalities permits the OID to capture one or more of reflectance images, absorption spectroscopic images, fluorescence images, and laser speckle contrast imaging (LSCI) images with or without mydriatic agents.

A number of imaging modalities have been developed that may be of relevance for ophthalmic imaging. These include:

(a) Laser speckle contrast imaging. When images are acquired under coherent (i.e., laser) illumination through an appropriately sized aperture, speckle patterns are formed. The blurring of speckle patterns due to motion can be mathematically estimated using a metric called speckle contrast, defined as the ratio of standard deviation of pixel intensities to the mean value of pixel intensities within a specified neighborhood of every pixel under consideration in the stack of images. The said neighborhood may be of different types and lie in the spatio-temporal domain, as described in Rege A, Senarathna J, Li N, Thakor N V (2012) "Anisotropic processing of laser speckle images improves spatiotemporal resolution", *IEEE Trans Biomed Engr*, vol. 59, no.5, pp. 1272-1280.

(b) Spectroscopic imaging. When images acquired under different illumination wavelengths are compared, it is possible to highlight features based on differential absorption, transmission, and reflection of light by different tissue/cell types. For example, differential analysis under near-infrared and green light can distinguish between oxygenated and deoxygenated blood.

(c) Reflectance imaging. This imaging mode is equivalent to photographing the eye under illumination that is similar to ambient light (e.g., light from a flashlight, light from a halogen lamp, etc.). These images also contain information analogous to spectroscopic images, since white light intrinsically contains multiple wavelengths of light. Oxygenated blood (in arteries under normal conditions) appears faint on a grayscale image obtained under white light illumination, while deoxygenated blood (in veins under normal conditions) appear darker.

(d) Fluorescence imaging. If a fluorescent dye is injected in the blood vessels, then high contrast images of blood vessels could be obtained using appropriate illumination wavelengths and optical filters.

Imaging the retina and/or the choroid poses a number of technical and practical challenges:

(a) Given the constraints placed by motion artifact on the camera exposure time in non-stabilized photography, ambient light does not provide adequate illumination for photographing the retina. Very little amount of light is captured by the camera sensor within the small exposure time, limiting its ability to achieve high contrast between retinal features. Thus, additional illumination from an external light source is generally needed.

(b) The geometry of the eye—specifically, the location of the retina, the pupil (and iris), the cornea and lens—does not provide enough leeway for the illumination and imaging paths to be along significantly different directions. This problem has been partially solved in the past using an optical assembly known as a fundus camera. However, the fundus camera cannot perform laser speckle contrast imaging, a method of imaging blood vessels and blood flow.

(c) Incidence of the illuminating light, especially coherent light (i.e., laser) on the retina may be harmful, thus placing a stringent constraint on the amount of energy that can be delivered to the retina to provide illumination for imaging purpose. Conventional retinal imagers that use lasers (e.g., scanning laser ophthalmoscopes) ensure through scanning that the laser illuminates a small region of interest (ROI) for a very short period of time, thus restricting the energy delivered to the retina despite using a beam of high power and intensity. Laser speckle contrast imaging (LSCI) involves simultaneous illumination of a field of view (FOV) as opposed to spot illumination and scanning—for longer periods of time in comparison to prior laser-based retinal imaging techniques. The overall illumination time could be as long as 10 seconds. Thus, a low-power laser whose power may be duly attenuated further must be used; and the activation and deactivation of the laser module must be controlled using a mechanical shutter or an electronic switch.

(d) Current retinal imagers place a significant socio-economic burden on its use. The high cost of individual components that make up the retinal imager, makes the overall system expensive. Combining the cost of the device with the additional cost of the eye-care specialists required to perform the procedure drives up the cost of eye exams and overall healthcare expenditures. Further, most retinal imagers require chemically-induced pupil dilation to capture a large FOV, which makes their use complicated and inconvenient.

In some embodiments, the OID can be configured with an illumination scheme that provides for off-center transmission of light through the cornea and lens. Providing illumination light along an optical axis of the OID may cause the illumination light to strike the cornea and/or lens at an angle normal to their surface such that the light may partially reflect back along the optical axis towards the imaging optics, creating artifacts or otherwise interfering with imaging of the fundus. Accordingly, this disclosure describes optics that can be employed to transmit light through the cornea and lens while reducing the amount of light striking the cornea and lens on or near the optical axis. Light can be transmitted to and through the cornea and eye lens in a number of shapes including shapes that are substantially annular (ring shape) or polygons on either side of the optical axis while avoiding light striking the cornea and/or lens on or near the optical axis at angles normal to the surfaces of the lens and cornea. Therefore, off-center transmission of light, in this context, implies that the light is either generally directed towards the cornea along an axis is not aligned with the optical axis of the eye, or substantially annular such that irrespective of the relative orientations of the illumination axis and the optical axis of the eye, the illumination beam does not significantly illuminate the region of the cornea that would reflect light back to the camera.

In the case of incoherent light illumination, due to its tendency to diffuse more than coherent light, preventing light from striking the cornea and lens on or near the optical axis can sometimes be achieved by simply introducing an obstacle somewhere along the optical axis of the path of the light between the incoherent light source and the lens. For example, an image of the round obstacle can be focused on the cornea as a dark disk in the center of the cornea surrounded by a bright ring. Once the ring of incoherent light passes through the cornea and lens, it will tend to diffuse as it passes through the eye and illuminate the fundus at least somewhat uniformly. Incoherent light, however, is not suitable for performing certain types of imaging of the fundus, including laser speckle contrast imaging (LSCI), which requires coherent light.

With coherent light, however, simply introducing an obstacle along the optical axis is not sufficient to block light from striking the cornea on axis while also adequately illuminating the fundus substantially uniformly across a field of view. Rather, when striking the cornea, the coherent light will tend to reproduce the shape of the obstacle, whether annular, polygonal, or some other shape.

This disclosure therefore proposes several techniques for transmitting light to the eye in a manner that avoids light striking the eye along the optical axis, thereby reducing reflections traveling back along an imaging light path, while also providing substantially uniform illumination of a region of interest of the fundus. In some embodiments, an OID can include one or more axicon lenses configured to shape a coherent light beam that focuses to an annular shape on the cornea and lens and then spreads to effect substantially uniform illumination of the fundus. An axicon lens is a lens that has a conical surface and can transform a laser beam into a ring-shaped distribution of light. In some embodiments, an OID can include one or more cylindrical lenses configured to transform a laser beam into rectangular bars of light on the cornea on either side of the optical axis. The rectangular bars can spread out as they traverse the inside of the eye to create an illumination pattern of two adjacent or slightly overlapping rectangular bars on the fundus, thereby illuminating the region of interest substantially uniformly. In some embodiments, an OID can include additional optical components configured to reduce reflections of coherent and incoherent light from reaching an image sensor or camera module of the OID. For example, the OID can pass the light through a first polarizer in the illumination optics before introducing the light into the eye. A second polarizer can be used in the imaging optics to block light having a certain polarization. Polarized light reflected by surfaces in the illumination path and/or surfaces in the eye including the cornea, lens, and back of the retina, will retain its polarized state and get blocked by the second polarizer, whereas light scattered by the fundus will have random polarization, and thus some of it will pass through the second polarizer and continue through the imaging optics to the image sensor of the OID.

The OID can be used both in the clinic and the laboratory to image the tissue of the eye of humans and animals to provide quantitative anatomical and physiological information for assessment of tissue function and management of correlated diseases. Imaging of the tissue of the eye includes, for example, the imaging of anatomical features of the retina and choroid (e.g., the location, length, density, and type of blood vessels) and associated physiological parameters (e.g., blood flow rates, oxygenation, hematocrit, and changes in diameter, length, density, oxygenation, and hematocrit) that indicate retinal function. The OID can also image blood, as in the case of hemorrhages and blood leakage resulting from blood vessel proliferation and damage. Thus, the OID can be used to monitor the retinal anatomy and physiology for research and diagnosis of a number of pathophysiologies (e.g., DR, HR, ROP, AMD, CNV, and retinal detachment). The OID can be designed either as different embodiments that are customized for the application but employ the principles disclosed herein, or as a single embodiment that contains adjustable components providing for use in both humans and animals and for one or more diseases or conditions.

The OID can also be utilized to monitor efficacy of medical interventions in the eye during and after the procedure. Such interventions might be surgical (e.g., laser photocoagulation surgery or vitreoretinal surgery) or chemotherapeutic (e.g., use of an anti-VEGF drug in the eye or investigation of eye drops). The OID can be used as a real-time or near-real-time feedback mechanism during, for example, any surgical procedure where monitoring of vascular changes would be of relevance. To illustrate this example, the OID can present the real-time LSCI images and blood flow parameters in front of the surgeon's eye using a display mechanism built into a glasses-like device worn by the surgeon or using some physical or virtual screen viewable by the surgeon. The OID can be used as a therapy-planning tool (i.e., to guide medical interventions). For example, the OID can identify specific blood vessels that are candidates for laser photocoagulation surgery in the eye and this information can be presented to the surgeon for consideration. The OID can be used as a therapy control mechanism to automatically control, for example, a computer-guided laser for blood vessel photocoagulation or to trigger the delivery or prescription of a specific medication. The OID can also be used for therapy-planning in a manner that allows the therapy to avoid certain types of blood vessels.

The OID can be used to detect non-ophthalmic diseases or conditions. These diseases or conditions can be organ-specific or systemic. For example, the OID can be used for early diagnosis or risk assessment of conditions like stroke and other types of brain lesions or conditions. Similarly, systemic disease (e.g., heart disease or diabetes) can be diagnosed and monitored based on an evaluation of the anatomical and physiological information obtained with the OID (e.g., changes in retinal blood flow rates).

Finally, the OID can be incorporated into an electronic health records (EHR) system or a mobile disease management system as a feedback mechanism to improve diagnosis or treatment of the specific disease target. For example, the OID can automatically store the images obtained into the patient's EHR for subsequent viewing and analysis. In addition, the OID can automatically make notations in the EHR indicating a number of important health information (e.g., the date of the most recent eye exam, the risk level for a specific disease, and the specific values of physiological parameters indicative of the disease). The OID can also produce a report of this information that can be incorporated into an EHR or other similar system and/or transmitted to an appropriate healthcare provider, caregiver, or the patient.

An example of incorporating the OID into a mobile disease management system is for early diagnosis and associated management of DR, a complication of diabetes with symptoms in the eye. Diabetes and its progression could be tracked through routine monitoring of the eye using the OID and subsequent incorporation of the data into an EHR report. Such data can be stored in a time-stamped manner, and blood vessel information (e.g., vessel diameter and blood flow) could be compared through graphs, image overlays, difference images, and other visualization methods. Such data (and associated comparative analyses) could be made available to physicians and specialists for a more detailed understanding of the history and current state of the disease, so that custom care can be provided.

According to some embodiments, an OID includes: A) an illumination module comprising one or more illumination sources at least one of which is produces coherent illumination such as a laser; B) one or more imaging sensors configured to collect light from the one or more regions at the back of the eye that are imaging targets; C) an illumination optical assembly including one or more optical elements configured to direct light from the illumination module to one or more imaging targets within the eye such that the illumination on the retinal or choroidal tissue is uniform or substantially uniform and does not generate a glare or a substantial glare at the camera sensor because of reflection from the anterior structures of the eye such as the cornea and the lens of the eye; D) an imaging optical assembly including one or more optical elements configured to direct light from the one or more imaging targets within the eye to the one or more imaging sensors such that the one or more imaging sensors may be focused on the imaging targets; E) means to do one or more of collecting, processing, storing, visualizing, and sharing of data that is acquired by the one or more imaging sensors and may also include data pertaining to the configuration of the OID during imaging; and F) a means of controlling imaging parameters that may include adjusting illumination characteristics, image acquisition characteristics, image processing characteristics, image storage characteristics, image visualization characteristics, image sharing characteristics, and the optical arrangement; wherein the one or more imaging targets refer to specific regions of tissue at the back of the eye that are of interest for imaging and may include portions of the retina and the choroid.

According to some embodiments, the OID may be configured for implementing laser speckle contrast imaging (LSCI) and producing "LSCI output data". LSCI refers to the imaging of speckle patterns caused by laser light scattered by the tissue, and the subsequent processing of these speckle patterns to assess blurring in the imaged speckle patterns to obtain information about movement of the scattering particles. Therefore, LSCI is able to produce information pertaining to blood flow in the imaged tissue, and because blood flow is often restricted to blood vessels in tissue, LSCI is also able to map out blood vessels in tissue. LSCI output data refers to resulting information that can be obtained by processing the image data acquired by the one or more imaging sensors and may include one or more of images, videos, numerical data, plots and graphs, comparisons, and decisions.

In embodiments of OID configured for LSCI: A) the illumination module comprises at least one laser source with a substantially constant wavelength during image acquisition that produces LSCI output data; B) the one or more imaging sensors comprise a camera that can acquire image data at one or more specified exposure times; C) the illumination optical assembly is configured to obtain laser illumination on the imaging target that is substantially uniform spatially and over time; D) the imaging optical assembly is configured to focus the imaging target on the camera and to include an aperture in the path of light from the imaging target to the camera that results in the production of a speckle pattern on the camera; and E) one or more processors are configured to process the acquired image data and characterize the extent of blurring of the speckle pattern in the spatial and/or the temporal domains and generate LSCI output data.

In embodiments of OID configured for LSCI, the illumination optical assembly is configured to substantially avoid direct reflection back to the camera from the anterior structures of the eye such as the cornea and the intraocular lens (IOL) while still illuminating the regions of interest in the posterior section of the eye with substantial spatial uniformity and substantial uniformity over time. This is achievable through the use of lenses that do not concentrate light from a parallel beam to a substantially pointed focus. One example of such a lens is an axicon lens that has at least one surface that is conical and therefore, the axicon lens concentrates light from a parallel beam to a ring rather than a point. Another example of such a lens is a cylindrical lens that is curved along one dimension but not curved along its perpendicular dimension, and therefore, the cylindrical lens concentrates light from a parallel beam to a line (segment) rather than a point. The advantage of concentrating (converging) laser light to a ring-shaped or a line-shaped cross-section en route to illuminating the retina is that if the ring or line focus coincides with or is in the proximity of the cornea or the IOL, the substantial lack of illumination at the center of the illumination axis (which is also the imaging axis) will prevent direct reflection from the cornea and IOL towards the camera. Light reflected from portions of the cornea and IOL that are illuminated by the ring-shaped or line-shaped cross-section of the laser beam does not reach the camera because of the convex curvature of the cornea and IOL. Past its focal plane, the light diverges to eventually illuminate the retina and choroid with uniformity.

In embodiments of OID configured for LSCI, the imaging optical assembly is configured to include at least one aperture that determines the speckle characteristics (Airy disc diameter) in conjunction with the optical magnification of the OID and the wavelength of the laser used. The diameter of the aperture may be fixed or adjustable, but may not be adjusted during acquisition of a single data set that is used to generate LSCI output data. The aperture diameter may be chosen (by selectively engaging a specific aperture among many), or pre-adjusted prior to image acquisition such that characteristics of the speckle pattern (e.g., the diameter of the Airy disc) are not influenced by the size of the pupil of the eye that is being imaged, and the diameter of the Airy disc is between one and five times the size (edge) of the camera pixel. The latter criterion enables effective spatial sampling while imaging the speckle. To prevent the aperture from blocking off significant amount of the imaging field of view or the amount of light returning from the back of the eyes, it is useful to include the aperture at a location in close proximity to the image of the pupil of the eye generated by the portion of the imaging optical assembly that lies between the pupil of the eye and the aperture.

In embodiments of OID configured for LSCI, some optical elements may be encountered in the path of illumination from the illumination source to the fundus of the eye as well as in the path of the imaging rays from the fundus of the eye to the image acquisition module. An example of such an optical element is the objective lens, which may be a single lens or a lens assembly separated by glue, air or other optical media. The position of the objective lens may be fixed or adjustable. Adjustments of the objective lens position may allow for focusing and may also compensate for the refractive errors or state of accommodation of the imaged eye.

In embodiments of OID configured for LSCI, a beam splitting element may be used to enable the illumination and imaging light to be substantially co-axial when passing through the iris of the imaged eye, while still using separate optical elements to shape and control the illumination and a separate set of elements to form an image of the fundus on the camera sensor. The beam splitting element may be replaced with a mirror that that has a provision for achieving the same function because of its tilt, its position relative to the illumination and imaging axes, its size, or its shape.

In embodiments of OID configured for LSCI, some or all optical elements may have anti-reflective coatings to reduce glare and stray reflections from the optical elements themselves.

In embodiments of OID configured for LSCI, the one or more processors are configured to receive from the camera image data comprising speckle images and compute metrics that estimate the extent of blurring in the speckle pattern caused by moving scatterers. One such metric is laser speckle contrast, and is defined at any pixel of interest as the coefficient of variation of pixel intensities within the local neighborhood of the pixel of interest. The local neighborhood around the pixel of interest may be defined in (a) the spatial domain, that is, a collection of pixels around the pixel of interest and which lie within the same capture speckle image; or (b) the temporal domain, that is, a collection of pixels at the same location in each of multiple speckle images acquired sequentially; or (c) in the spatio-temporal domain, that is, a collection of pixels around the same location in each of multiple speckle images acquired sequentially. The local neighborhood of pixels may be isotropic, semi-isotropic, or anisotropic, that is, within a speckle image frame, the collection of pixels may lie in a circular window, a square window, or a line respectively. Other metrics that may offer substantially comparable information as the coefficient of variation may also be used to quantify the speckle blurring. Example of other metrics include correlation coefficient, cross-correlation, and normalized error. The speckle contrast is related to the velocity and volume of moving scatterers and therefore, may be used to estimate velocity or flow rate of blood. Velocity or flow estimation at each pixel may be carried out using mathematical functions or via the use of look-up tables to obtain a blood flow velocity index at each pixel.

In embodiments of OID configured for LSCI, the one or more processors are further configured to generate LSCI output data and render LSCI output data on a display unit for visualization. LSCI output data presents velocity of flow information pertaining to the region of interest that was imaged. According to one embodiment, the visualization on a digital display (monitor) comprises of laser speckle contrast values at each pixel mapped in pseudo-color to generate a map of the blood flow velocity index in the imaged region of interest. Mean or median blood flow velocity indices may be computed within specified regions and numerical or graphical visualization of blood flow velocity indices or their regional aggregates may be displayed. Numerical or graphical representation of the trend in blood flow velocity indices over time may be presented. The raw or processed data may be transmitted to the display unit via wired or wireless means. The display unit may reside in physical proximity to the other components of the OID or be located remotely and accessed via the internet or a local area network.

In embodiments of OID configured for LSCI, the one or more processors are configured to receive from the camera image data comprising speckle images, and store the received image data. The one or more processors may be configured to store LSCI output data after it has been generated. The one or more processors may be configured to store the configuration information and parameters that were used in generating the LSCI output data. Any data may be stored locally, that is, at storage locations such as internal or external, fixed or removable memory devices that are physically connected to the processor; or remotely, that is, at storage locations that require the internet or a local area network to access. Therefore, raw or processed data may be transmitted to a storage destination by wired or wireless means.

In embodiments of OID configured for LSCI, a gaze fixation mechanism may be used for the purpose of stabilizing the subject's gaze during an image acquisition session. The gaze fixation mechanism may be on-device; that is, physically attached to the OID, or off-device, that is, physically not attached to the OID. The gaze fixation mechanism may be configured such that a target is available to be viewed by the imaged eye or such that a target is available to view by the contralateral (non-imaged) eye. The target on which the eye is expected to fixate its gaze upon, may be a real object, or a real image of an object, or a virtual image of an object. The gaze fixation mechanism can include an optical assembly consisting of one or more optical elements, wherein the one or more optical elements include lenses, filters, mirrors, collimators, beam splitters, fiber optics, light sensors, and apertures. The gaze fixation mechanism can include one or more kinematic elements to adjust one or more optical elements. The gaze fixation mechanism projects an image of a physical or virtual object at a specified target location with respect to the imaged eye or the contralateral eye, wherein the projected image can be determined prior to or at the time of imaging and the projected image location varies during the course of imaging to facilitate acquisition of images of different regions of the eye. The gaze fixation mechanism can further include a display unit that generates one or more virtual objects, the projected images of which coincide with the intended target for gaze fixation. The gaze fixation mechanism can further include a processing element to control operation of the gaze fixation mechanism and to perform one or more calculations for the operation of the gaze fixation mechanism, wherein the one or more calculations include calculations pertaining to location identification of the intended target of gaze fixation and location identification of the virtual or physical object.

In some implementations, the OID can be configured to perform multimodal imaging using both coherent light and non-coherent light. Such an OID can include a second light source configured to emit non-coherent light and an obstacle configured to block a portion of the non-coherent light. The coherent and non-coherent light paths can be combined using a beam splitter element configured to receive the non-coherent light from a fourth direction and the coherent light from a fifth direction, and transmit the non-coherent light and the coherent light in a sixth direction towards the first beam splitter.

According to some embodiments, the OID may be configured to implement one or more of LSCI, spectroscopic imaging, reflectance imaging, and fluorescence imaging by selecting the appropriate illumination type, and commensurately appropriate image acquisition and processing methods.

For implementing any of spectroscopic imaging, reflectance imaging, or fluorescence imaging, the illumination module of the OID may use the aforementioned means of using an axicon or cylindrical lens in the illumination path to avoid illuminating the cornea and IOL along the illumination and imaging axes. However, if the illuminating light is not coherent, the same effect may be obtained by placing an obscuration centrally on the illumination axis at a location along the illumination path that corresponds to an image of the cornea or the IOL that would be formed by the optical elements between the cornea or IOL and the obscuration location. Thus, a sharp and dark image of the obscuration would be formed on the cornea or IOL preventing substantial reflection that reaches the one or more image sensors. Beyond the image, the non-coherent light does not remain strongly collimated and diffuses rapidly to create substantially uniform illumination. It is noteworthy that this mechanism is not suitable when the illuminating light is a laser because its coherence and collimation project the obscuration in the divergent path of the light from the cornea to the retina.

For implementing any of spectroscopic imaging, reflectance imaging, or fluorescence imaging, embodiments of the OID may contain substantially similar configurations of the illumination module, illumination optical assembly, imaging optical assembly, and the image acquisition module or may be modified to accommodate imaging requirements.

For implementing any of spectroscopic imaging, reflectance imaging, or fluorescence imaging, embodiments of the OID may contain substantially similar optical elements including beam splitting elements, mirrors, polarizers, filters, with or without anti-reflective coatings, or may be modified to accommodate imaging requirements.

For implementing spectroscopic imaging, the OID engages an illumination module comprising a means of generating illumination of at least two different wavelengths and recording wavelength-specific images of the target tissue. Wavelength-specific images correspond to images acquired by the one or more image sensors when light within a narrow band of wavelengths expose the sensor. Spectroscopic imaging pertains to the capture of multiple wavelength-specific images at least two of which are obtained from light of different wavelengths. Illumination at each of the at least two different wavelengths may be produced at either at the same time, at overlapping times, or at different non-overlapping times such as in quick succession. The illumination may be achieved by multiple sources, each of which emits light within a narrow band of wavelengths; or by the use of a tunable source of light that emits light within a narrow band of wavelengths at a time, but the said narrow band may be selected and set to be different over a much broader range of wavelengths; or by the use of a broadband source of light that emits composite light comprising more than one wavelengths at a time. Illumination at a specific wavelength (that is, within a narrow band of wavelengths) may also be achieved through the use of chromatic optical filters in the illumination path. The OID engages one or more image sensors that possess reasonable sensitivity to light at the wavelengths of the illumination employed. The imaging optical assembly of the OID may use a filter to selectively pass light with the desired wavelength. A filter element can be used in the imaging optical assembly if a broadband illumination source is used and there is no filtering or wavelength discriminating mechanism in the illumination module or the illumination optical assembly. A single image sensor may receive each of the multiple wavelength-specific images sequentially in time, or multiple sensors may be employed in an arrangement wherein each sensor is selectively or preferentially sensitive to light of different wavelength. Differential sensitivity of the imaging sensor may be a result of sensor construction or the differential guidance of light with different wavelengths to different imaging sensors.

For implementing spectroscopic imaging, the OID uses a processor that is configured to differentially compare pixel intensities of the same region across the multiple wavelength-specific images. The amount of light absorbed and reflected at multiple wavelengths provides insights into the possible concentration of specific materials in the target tissue because the absorption and reflection characteristics of these materials are well known. Materials that are biologically important are oxy-hemoglobin, deoxyhemoglobin, water, and other constituents of tissue including cytochrome C. The one or more processors of the OID may be employed to analyze the wavelength-specific images and the features contained within the wavelength-specific images either individually or together, to produce "spectroscopic output data". Spectroscopic output data comprises one or more of images, videos, graphs, plots, numerical information, comparisons, and decisions obtained by processing spectroscopic images.

For implementing reflectance imaging, the OID uses an illumination module comprising a means of generating either broadband or narrow band illumination and one or more imaging sensors to record images of the target tissue under either of these illuminations. To obtain a sharp image without much blurring because of motion artifact, a high intensity illumination may be used over a short duration of time (e.g., a light flash) and the light returning from the target tissue be captured by the one of more image sensors synchronously. The one or more processors of the OID may be employed to further enhance the image and the features contained within the image to produce "reflectance output data". Reflectance output data comprises one or more of images, videos, graphs, plots, numerical information, comparisons, and decisions obtained by processing reflectance images.

For implementing fluorescence imaging, the OID uses an illumination module comprising a means of generating a narrow band illumination that excites the fluorophore in the target tissue, and a high quality narrow band optical filter in the imaging optical assembly to suppress the illuminating light at the excitation wavelength from reaching at least one imaging sensor while permitting the fluorescent emission, that is, light at the emission wavelength, to reach that at least one imaging sensor so that an image of the fluorescing material may be captured. To obtain a sharp image without much blurring because of motion artifact, a high intensity illumination may be used over a short duration of time (e.g., a light flash) and the light returning from the target tissue be captured by the one of more image sensors synchronously.

The OID can further include one or more processors configured to control the arrangement of the one or more optical elements, to control durations, duty cycles, and synchrony of the plurality of illumination modalities and the one or more imaging sensors, to control one or more image acquisition parameters, or to process data generated from the one or more imaging sensors to perform one or more of laser speckle contrast imaging, spectroscopic imaging, reflectance imaging, and fluorescence imaging. The one or more optical elements of the optical assembly can be configured to direct light to the one or more regions of tissue of the eye can include one or more spectrally selective filters configured to restrict the illumination from the one or more sources of incoherent illumination to one or more narrow bands of light, wherein the narrow bands of light include green light, blue light, red light, and near infrared light. The OID can further include one or more neutral density filters configured to attenuate the illumination power of the one or more sources of coherent or incoherent illumination. The OID can further include one or more filters configured to reject harmful wavelengths for a specific application. The light directed to the one or more regions of tissue of the eye can include one or more illumination beams generated from the illumination module. The one or more illumination beams can be coaxial with the optical axis of the imaging path. The one or more illumination beams can be not coaxial with the optical axis of the imaging path. The light directed to the one or more regions of tissue of the eye from the one or more illumination beams can occur synchronously or asynchronously.

In some implementations, the OID can include a processor, or be included in a system having a processor, where the processor is configured to generate compound images from images taken using coherent and non-coherent light, respectively. Such and OID can include a processor configured to receive, from the image sensor, first data representing a first image taken with the coherent light and second data representing a second image taken with the non-coherent light. The processor can be configured to process the first data and the second data to generate a compound image.

According to some embodiments, the OID can further include one or more kinematic elements for engaging, indexing, or linear translation of the one or more optical elements, wherein the one or more kinematic elements includes stepper motors, rotors, gears, and guide rails. The OID can further include one or more means of user input, wherein the one or more means of user input includes one or more buttons, switches, touchscreens, physical or virtual keyboards, or means to control a cursor. The OID can further include one or more means of data transmission to uni-directionally or bi-directionally exchange information with one or more storage devices, display devices, or processing devices, wherein the one or more storage devices, display devices, or processing devices can be standalone or associated with one or more remote computers or servers. The one or more processors can be further configured to calculate laser speckle contrast values for pixels of the one or more imaging sensors associated with the one or more regions of tissue of the eye, wherein the calculated laser speckle contrast values use properties of a pixel's neighborhood of pixels in spatial or temporal domains. The one or more processors can be further configured to extract information from data received, wherein the extracted information includes estimates of blood velocity, estimates of blood flow, blood vessel diameters, spatial density of blood vessels, or classification of blood vessels as arterioles or venules. The one or more processors can be further configured to acquire an image stack and to register images of the acquired image stack to a reference image, wherein the reference image can be acquired independently or can be one of the images in the acquired image stack.

In some embodiments of the OID, the imaging optical assembly may be configured to include at least one objective lens configured to receive scattered coherent light from the fundus of the eye and converge the light rays into the imaging optical assembly for image formation on the camera sensor. Such an objective lens may also lie in the illumination path, and therefore, achieves the added functionality of guiding light for illumination of the fundus of the eye through its pupil. The OID can also include polarizers for reducing reflections of illumination light from interfering with image capture at an image sensor of the OID.

In some implementations, the OID can include optical elements that allow the objective lens to simultaneously adjust the illumination to be substantially uniform on the imaging field of view without back-reflection from anterior surfaces of the eye, and bring the imaging field of view into focus at the camera. In other words, both the illumination light and the scattered light can be brought into focus at the same time by adjustment of a position of the objective lens alone. The objective lens of such an OID, can form an image of the back of the eye at an imaginary plane or imaginary surface inside the OID. In doing so, the objective lens can also produce the same spatial illumination characteristics at the back of the eye, as the spatial illumination characteristics on said imaginary plane or imaginary surface. The objective lens, in conjunction with the imaging optical assembly can form an image of the iris of the imaged eye at an imaginary plane or imaginary surface inside the OID along the imaging path, near which the dominant aperture stop of the OID may be positioned. The objective lens, in conjunction with the illumination optical assembly can form an image of the iris of the imaged eye at an imaginary plane or imaginary surface inside the OID along the illumination path, near which the annular focus of the illumination may occur when the illumination module and illumination optical assembly are configured appropriately. The objective lens can thus be configured or adjusted to transform the scattered coherent light such that it illuminates the field of view at the back of the eye with substantial uniformity while being annular in cross-sectional profile as it passes through the pupil of the eye, and the emergent light is brought into focus on the camera sensor.

In some implementations, the OID can include polarizers for reducing reflections of illumination light from interfering with image capture at an image sensor of the OID. The OID can thus include a first polarizer that is positioned in the illumination path between the illumination source and the objective lens where the first polarizer is configured to pass light having a first polarization state, and a second polarizer positioned in the imaging path between the objective lens and the image acquisition module where the second polarizer is configured to pass light having a second polarization state different from the first polarization state.

In some implementations, the OID can include a gaze fixation mechanism to aid the patient in maintaining a stable eye position during imaging. Such an OID can include a gaze fixation target configured to emit target light, and combine the coherent light and the target light using a second beam splitter configured to receive the target light from a fourth direction and the coherent light from a fifth direction, and transmit the target light and the coherent light in a sixth direction towards the first beam splitter.

According to some embodiments, the OID can further include an immobilization mechanism for stabilization with respect to the subject's eye, wherein the immobilization mechanism can include one or more optical elements and one or more rigid components, wherein the one or more optical elements includes lenses, filters, mirrors, collimators, beam splitters, fiber optics, light sensors, and apertures and the one or more rigid components includes a helmet or one or more nose bridges, sunglasses, goggles, rubber cups, and helmets. The disease management system, can further include: A) one or more OIDs configured to perform one or more of laser speckle contrast imaging, spectroscopic imaging, reflectance imaging, and fluorescence imaging of one or more regions of tissue of the eye, wherein the one or more regions of the tissue of the eye include the retina, choroid, the cornea, the sclera, and the eye lens; one or more sensors configured to collect at least one type of patient-specific data. The disease management system can further include: one or more processors configured to process the anatomical or physiological information from the one or more regions of tissue of the eye and the at least one type of patient-specific data; and one or more interface devices configured to display the at least one type of patient-specific data and to allow the user to input information to change the functionality of the one or more processors. The one or more OIDs can be configured for one or more diagnostic, prognostic, or therapeutic purposes, wherein the one or more diagnostic, prognostic, or therapeutic purposes include ophthalmic and non-ophthalmic diseases or conditions. The one or more sensors consists of ophthalmic or non-ophthalmic sensors. The processor can be configured to read and analyze the at least one type of patient-specific data from one or more points in time, wherein the analysis includes comparing the at least one type of patient-specific data to one or more thresholds, comparing the at least one type of patient-specific data at different points in time, calculating trends of the at least one type of patient-specific data, comparing trends of the at least one type of patient-specific data to one or more thresholds, extrapolating trends of the at least one type of patient-specific data to estimate the expected future values of the at least one type of patient specific-data, and computing one or more threshold criteria based on population-based statistics associated with the one or more patient-specific data. The one or more thresholds include one or more constant values or values that depend on the attributes of the at least one type of patient-specific data, or values that depend on population-based statistics associated with the at least one type of patient-specific data. The at least one type of patient-specific data includes one or more electrocardiograms, blood pressure measurements, heart rate measurements, pulse oximetry measurements, blood glucose measurements, hemoglobin A1c measurements, ocular pressure measurements, respiratory measurements, plethysmograms, weight measurements, height measurements, age, body position, electroencephalograms, electrooculograms, electroretinograms, visual evoked responses, prior medical history, and information derivative to the at least one type of patient-specific data. The processor can be configured to: trigger one or more types of therapy through one or more manual, semi-automatic, or automatic means; and facilitate the communication of the at least one type of patient-specific data to one or more devices for storage, display, or analysis.

According to some embodiments, a method of imaging a region of tissue of the eye, includes: configuring the OID for image acquisition suitable to achieve the desired imaging modality, wherein the configuring step includes maintaining a pre-configured state, adjusting one or more optical assemblies, illumination modalities, and image acquisition parameters; initiating illumination generated by the OID; initiating image acquisition based on the image acquisition parameters; storing the acquired images; processing the acquired images; and changing manually or through the configured processing element of the OID, the source of coherent or incoherent illumination and repeating one or more of the adjusting the optical assembly, setting values for image acquisition parameters, initiating illumination, initiating image acquisition, storing, or processing steps.

According to some embodiments, the method can further include immobilizing an OID with respect to a subject's eye. The method can further include instructing the subject to fixate the gaze of the eye on a physical or virtual object. The OID can be configured to acquire images using a plurality of imaging modalities, wherein the plurality of imaging modalities includes laser speckle contrast imaging, spectroscopic imaging, reflectance imaging, and fluorescence imaging. The OID can be handheld and immobilized by resting or pressing against the subject's face or eye. The OID can be used in conjunction with eyeglasses, goggles, a helmet, or other accessory to immobilize the OID with respect to the subject's head or eye. The OID can be used in conjunction with a chin rest or other accessory to immobilize the subject's head or eye. The virtual object can be generated by the OD and the location of the virtual object can be predetermined or determined dynamically by an operator. The optical assembly of the OID can contain one or more optical elements that can be adjusted manually by the operator, semi-automatically, or automatically by a processor. The image acquisition parameters can include exposure time, gain, pixel sensitivity, number of images, frame rate, timing sequence, pixel resolution, pixel area, and image magnification. The illumination generated by the OID can include light from one or more coherent illumination beams and light from one or more incoherent illumination beams. Storing the acquired images can include recording one or more images on a local or remote storage device, wherein the storage device includes any one or more of random access memory, magnetic or solid state hard disk technology, flash disk technology, or optical disk technology. The processing of acquired images can include registration of acquired images, processing for laser speckle contrast imaging, feature extraction using a combination of one or more of laser speckle contrast images, spectroscopic images, reflectance images, and fluorescence images, processing for spectroscopic imaging, and preparing images or processed images for communication, storage, or display.

According to some embodiments, a method of analyzing images obtained using an OID includes: selecting the one or more images and parameters to analyze; selecting the one or more processing algorithms to perform; triggering the one or more processing algorithms; and presenting the output of the one or more processing algorithms.

According to some embodiments, the one or more images can be generated from one or more of laser speckle contrast imaging, spectroscopic imaging, reflectance imaging, and fluorescence imaging. The one or more parameters can be one or more of anatomical and physiological parameters extracted from one or more images generated from one or more of laser speckle contrast imaging, spectroscopic imaging, reflectance imaging, and fluorescence imaging. The one or more parameters can be extracted from one or more sensors and includes electrocardiograms, blood pressure measurements, heart rate measurements, pulse oximetry measurements, blood glucose measurements, hemoglobin A1c measurements, ocular pressure measurements, respiratory measurements, plethysmograms, weight measurements, height measurements, age, body position, electroencephalograms, electrooculograms, electroretinograms, visual evoked responses, prior medical history, and information derivative to the one or more parameters. The output can include one or more visual renditions of the one or more images, the one or more parameters, thresholds, trends, and information derivative to the one or more parameters. The method can further include one or more interface devices configured to allow an operator to manipulate one or more of the selecting of the one or more images and parameters to analyze, the selecting of the one or more processing algorithms to perform, the triggering of the one or more processing algorithms, and the presenting of the output of the one or more processing algorithms. The method can further include triggering therapy manually, semi-automatically, or automatically based on the one or more analyzed images or parameters. The therapy includes one or more of a recommendation to the user to change a specific drug medication or to perform some other treatment procedure, a recommendation that allows the user to trigger an automatic treatment or procedure, or an automated signal that controls a treatment mechanism.

According to some embodiments, a method of managing a patient's disease includes: acquiring one or more images of one or more regions of the tissue of the eye using an OID; acquiring at least one type of patient-specific data from one or more sensors; processing the one or more images, one or more parameters, and at least one type of patient-specific data; and presenting the processed information for review by a caregiver.

According to some embodiments, the OID can be configured to generate the one or more images from one or more of laser speckle contrast imaging, spectroscopic imaging, reflectance imaging, and fluorescence imaging. The method can further include triggering therapy manually, semi-automatically, or automatically based on the one or more processed information.

In some implementations, the OID can be configured to perform multimodal imaging using both coherent light and non-coherent light. Such an OID can include a second light source configured to emit non-coherent light and an obstacle configured to block a portion of the non-coherent light. The coherent and non-coherent light paths can be combined using a second beam splitter configured to receive the non-coherent light from a fourth direction and the coherent light from a fifth direction, and transmit the non-coherent light and the coherent light in a sixth direction towards the first beam splitter.

According to some embodiments, the OID can include one or more lenses for providing illumination that enters the eye in a manner that avoids illuminating a center of the cornea and/or eye lens before spreading to provide substantially uniform illumination to a field of view of the fundus. For example, an OID can employ one or more cylindrical lenses to create a rectangle of illumination on either side of the center of the cornea. Such an ophthalmic imaging device can include a first light source configured to emit two beams of coherent light and a cylindrical lens configured to receive the two beams of coherent light from the first light source and transform the two beams of coherent light such that they focus into two first rectangular shapes at a first imaging plane. The OID can include a first beam splitter configured to receive the two beams of coherent light from the cylindrical lens from a first direction and transmit it in a second direction. The OID can include an objective lens configured to receive the two beams of coherent light from the beam splitter and focus the two beams of coherent light into two second rectangular shapes at a second imaging plane substantially coinciding with a cornea of an eye. The objective lens further configured to receive scattered coherent light from a fundus of the eye, and the first beam splitter further configured to receive the scattered coherent light from the objective lens from the second direction and transmit it in a third direction. An imaging sensor can be configured to receive scattered coherent light from the beam splitter.

As described in more detail below, the OID is composed of a plurality of optical elements, illumination modules, cameras, photosensors, power sources, processor elements, storage elements, and communication elements. The specifications and parameters of the imager may change to accommodate differences in the subjects' eyes. For example, rat eyes (used in research) are much smaller in size that human eyes. The rat eye curvature is also different than the curvature of the human eye. Also, the apparatus may be embodied differently for different tissue being imaged. For example, imaging the choroid may require illumination at a higher wavelength than when imaging the retina. Likewise, imaging the cornea may require a different lens assembly than when imaging the retina. The apparatus may also be embodied with adjustable elements that can be moved and/or tuned for specific applications.

Some embodiments incorporate the OID into an external system for disease management and treatment. In some embodiments, the OID communicates with the external system through a wireless connection. In other embodiments, the OID communicates with the external system through a wired connection. In some embodiments, the OID is incorporated into the external system to present data for review and tracking by a healthcare provider. In other embodiments, the OID is incorporated into the external system to recommend specific treatment options. In other embodiments, the OID is incorporated into the external system to automatically control therapy.

These and other features of the OID are described in further detail below with reference to the accompanying drawings.

FIG. 1 is a schematic of components of an (ophthalmic imaging device) OID system 1400. In broad overview, the OID system 1400 includes components for illuminating the eye 1401, capturing images, and displaying the images. An illumination module 1405 generates coherent and/or incoherent light for illuminating the eye 1401. Illumination control optics 1410 convey the light to a beam splitting element 1415. The illumination control optics 1410 may manipulate the light with one or more lenses, mirrors, prisms, polarizers, or other optical components before transmitting the light to the beam splitting element 1415. A path of the light once transmitted to the beam splitting element 1415 may coincide with a path of scattered light returning from the eye 1401, so the illumination control optics 1410 can perform transformations on the light without affecting the scattered light. The beam splitting element 1415 transmits the light through the objective lens 1420, which transforms the light for transmission through the anterior structures and the optical opening of the eye 1401 (i.e., the cornea, pupil, and lens) and illumination of the fundus. The fundus scatters the light, and some of the scattered light exits the optical opening of the eye 1401. The objective lens 1420 receives some or all of the scattered light and transmits it to the beam splitting element 1415. The beam splitting element 1415 transmits the scattered light through imaging optics 1425 which focus the scattered light onto an imaging sensor 1430. The imaging optics 1425 may manipulate the scattered light with one or more lenses, mirrors, prisms, polarizers, or other optical components before transmitting the light to the imaging sensor 1430. The imaging sensor 1430, which can include a charge couple device (CCD) or an active-pixel sensor such as a complementary metal oxide semiconductor (CMOS) sensor, acquires one or more image frames, digitizes them, and sends the digitized image frames to the computer 1435, which can process the image frames and display a resulting image on the display 1440. As discussed previously, the OID system 1400 can employ multiple illumination and/or imaging modalities. For example, the OID system 1400 can perform laser speckle contrast imaging (LSCI), fluorescence imaging, spectroscopic imaging, and reflectance imaging. In some embodiments, the OID system 1400 can acquire and display images using a combination of modalities; for example, overlaying an LSCI image over a reflectance image.

The illumination module 1405 typically includes the following types of illumination and wavelengths:

(a) Red laser (narrow band within the approximate range: 625-655 nm)

(b) Green laser (narrow band within the approximate range: 520-545 nm)

(c) Blue laser (narrow band within the approximate range: 460-495 nm)

(d) Near infrared (NIR) laser (narrow band within the approximate range: 700-900 nm)

(e) Broadband white light illumination from LEDs, halogen lamps, etc.

(f) Red, green, blue or NIR light from appropriate LEDs or achieved by spectrally filtering white light (wavelength ranges, as indicated for lasers, above).

In an embodiment designed for LSCI, the illumination module 1405 in the OID system 1400 comprises one or more lasers or an equivalent coherent illumination source. In another embodiment designed for acquiring reflectance and/or fluorescence images or for viewing for interpretation or focusing (e.g., in preparation for image acquisition), the illumination module 1405 is one or more incoherent illumination sources.

Not all applications will require the use of all illumination sources or illumination modalities. For example, green illumination mode can be achieved by switching on a white light source with a green filter in the optical path and an appropriate neutral density filter to attenuate the intensity to the desired value. Such a green illumination mode may be provided in the OID system 1400 to provide the user/operator/interpreter with more information about the FOV. The OID system 1400 may not necessarily use this mode during every use/operation. Likewise, elucidation of microvascular flow in the retina may use a 785 nm (NIR) laser illumination to be invoked while segmentation of vessels into arteries and veins may use both the NIR laser as well as white illumination modes to be invoked sequentially.

The OID system 1400 may be used to perform fluorescence imaging, in which case the illumination module 1405 and associated spectral filter can depend on the dye being used. For fluorescein angiography, the illumination can be in the blue region of the electromagnetic spectrum, that is, its wavelength will lie in the range between 460 nm and 495 nm. For indocyanine green (ICG) angiography, the illumination may lie between 700 nm and 820 nm. Specific illumination patterns can be created by switching "on" and "off" the appropriate light source, together with pre-assembled, manual, or motorized control of filter sets.

The illumination module 1405 or illumination control optics 1410 or both may also contain one or more apertures (e.g., pinhole aperture, slit aperture, or circular apertures) of various sizes for finer control of illumination. Such an aperture may be fixed or adjustable, much like the filters described above. For example, one embodiment can incorporate an aperture wheel, analogous to the filter wheel, which can be rotated to invoke the aperture appropriate for the desired illumination mode. Another embodiment can incorporate adjacent apertures which can be slid into and out of position for a similar purpose.

The illumination module 1405 or illumination control optics 1410 or both can employ a combination of mechanical and electronic switching for enhanced control of one or more illumination sources. For example, the white light source may be switched "on" and "off" electronically, but red and green filters may be mechanically indexed in the path of the white light to achieve the red light illumination mode and the green light illumination mode respectively. A trigger for mechanical indexing or electronic switching or both may be manual, automatic, or semi-automatic. For example, in a manual embodiment, the user can rotate a spring-loaded indexing mechanism to selectively engage a first illumination source and orient it along an illumination axis, while simultaneously disengaging a second illumination source. In an automatic embodiment, a pre-set timing sequence or other control mechanism may be used to selectively engage each source for a fixed amount of time. Such a timing sequence may be provided to the switch circuit through a processor or to a motorized indexing mechanism. In a semi-automatic embodiment, the user can move a desired filter into position, then press a push button that causes one illumination source switch "off" after a period of time and another illumination source to switch "on".

In an embodiment that uses LSCI to image the retina, the OID system 1400 can be designed such that: (a) the illumination and imaging optical assemblies achieve illumination and imaging of the requisite field of view, (b) the light intensity at the retina does not exceed a safety threshold, (c) the desired imaging technique can be achieved through the subject's dilated or undilated pupil, and (d) the subject's pupil does not become critical in determining the speckle size (the diameter of the Airy disc pattern formed as a result of imaging through an aperture). To meet the objectives (a), (b) and (c), the numerical aperture of the illumination control optics 1410 should be commensurate with the required field of view. Therefore, focal length and diameter of the objective lens 1420 is chosen based on the angular field of view and the working distance (distance between the anterior-most surface of the eye and the front-most surface of the objective lens). In this embodiment, the illumination beam can converge at the pupil or substantially near the anterior structures of the eye, so that light is in its divergent phase beyond the pupil to illuminate the requisite field of view. A distance between the retina and the pupil is approximately in the range 17 mm-20 mm in human adults, and a beam diverging over this distance will decrease the risk of over exposure at the retina (than a beam that is convergent or parallel over the same distance). An undilated (and also unconstricted) pupil is assumed to be approximately 3-4 mm in diameter in human subjects.

In another embodiment, illumination of the entire FOV may be achieved through illumination of multiple smaller areas on the target tissue. Overlapping coherent illumination at the same time may cause interference, and therefore, the Illumination Control Optics 1410 and the Objective Lens 1420 may be adjusted such there is very little overlap (if any) in the coherent illumination. In case of non-coherent illumination, overlap of illuminated areas may be better tolerated. The multiple smaller areas may be illuminated and imaged sequentially in time, thus avoiding the complications of spatial overlap in illumination. The advantage of such an arrangement is to prevent the illumination beam from being centered at the imaging axis (called off-center illumination) so that back reflection from elements of the OID system 1400 or non-relevant portions of the target tissue (e.g., reflection from the cornea when the target tissue is the retina) is reduced, increasing contrast at the imaging sensor 1430. In one embodiment, annular illumination at the pupil is employed to achieve off-center illumination. In another embodiment, the illumination beam is split into multiple illumination beams, each of which is not coaxial with the imaging axis, and illumination control optics 1410 and objective lens 1420 can be utilized to focus each of these multiple illumination beams to converge at or in front of the pupil (e.g., on the focal plane) but not on the imaging axis as described above. In this embodiment, the resulting illumination of the FOV will be produced by the superposition of the individual and overlapping FOVs of each of these multiple illumination beams.

In some embodiments, the source of coherent illumination may be a diode laser, while in other embodiments, it may be one or more of diode laser, gas laser such as Helium Neon laser, vertical cavity surface emitting laser (VCSEL). Data obtained by the image acquisition module may be processed, stored, transmitted, or displayed. The processor may range in specifications and characteristics: it could be a miniature chip achieving one type of processing function or programmable to achieve multiple processing functions, it could be mobile or stationary, it could be described as a microcontroller, or a computer. The storage element may be magnetic or solid state hard disk, flash memory, memory cards (SD cards and similar technology), on-board memory on the processing element, be accessible via a local area or wide area network, or cloud-based storage accessible via the internet. The display may be a digital or analog display of any size and resolution capable of presenting image and numerical information. Any transmission of data may be achieved by wired or wireless means. Examples of wired transmission include transmission over the USB protocol (USB, USB 2.0, USB 3.0, USB 3.1), transmission over the Ethernet or gigabit Ethernet (gigE) protocol, transmission over the Firewire or IEEE 1394 protocol, transmission over the serial or parallel ATA protocols. Examples of wireless transmission include telemetry, Bluetooth protocols, Wi-Fi protocols, cellular network protocols such as 2G, 3G, Edge, 4G, LTE, 5G, and other means of near field communications. Data that is stored, transmitted, or displayed may also include data pertaining to the configuration of the OID such that image data captured by the OID can be processed and interpreted with context. Data may be stored, transmitted, or displayed at any point in time and at any processing step— before, during, or after processing. Similarly stored and transmitted data may be re-processed, re-stored in different formats, and re-transmitted for processing, storage, and display purposes.

Processing for LSCI. Speckle contrast may be calculated as the ratio of standard deviation and mean of pixel intensities in a neighborhood of pixels. The neighborhood of pixels around a pixel P may be derived from either or both of spatial and temporal domains, that is the pixels comprising the neighborhood may be spatially adjacent to the pixel P, or the pixels comprising the neighborhood may lie at the same location as P but in adjacent (in time) image frames, or the pixels comprising the neighborhood may lie both spatially adjacent to pixel P in the same frame and also in adjacent frames. The speckle contrast values may also be averaged either spatially or temporally. The neighborhood may be spatially isotropic, where the neighborhood may comprise the same number of pixel in every direction about the pixel P, or anisotropic, where the neighborhood may be preferentially oriented in one or more directions (e.g., along the direction of blood flow in vessels, or along the axial direction of blood vessels). Various ways of choosing neighborhoods and calculating laser speckle contrast is described in Rege A, Senarathna J, Li N, Thakor N V (2012) "Anisotropic processing of laser speckle images improves spatiotemporal resolution", *IEEE Trans Biomed Engr*, vol. 59, no. 5, pp. 1272-1280. The speckle contrast may be used, for example, to:

Obtain high-resolution images of blood vessels in the eye with high distinguishability from the background tissue, in healthy situations as described for brain vasculature in Murari K, Li N, Rege A, Jia X, All A, Thakor N V (2007) "Contrast-enhanced imaging of cerebral vasculature with laser speckle," *App Opt*, vol. 46, pp. 5340-6, as well as in abnormal situations as described for skin vasculature in Rege A, Murari K, Seifert A, Pathak A P, Thakor N V (2011) "Multi exposure laser speckle contrast imaging of the angiogenic microenvironment," *J Biomed Opt*, vol. 16, no. 5, p. 056006;

Obtain images of blood flow in the eye, as described for brain vasculature in Rege A, Murari K, Li N, Thakor N V (2010) "Imaging microvascular flow characteristics using laser speckle contrast imaging," in *Proc 32nd Ann Intl Conf IEEE Engr Med Biol Soc* (*EMBC*), *Buenos Aires*, pp. 1978-1981; and Obtain images of microvessel density in one or more regions of the eye, as described for brain tumor vasculature in Rege A, Seifert A, Schlattman D, Ouyang Y, Basaldella L, Li K, Tyler B, Brem H, Thakor N V (2012) "Longitudinal in vivo monitoring of rodent glioma models through thinned skull using laser speckle contrast imaging", *J Biomed Opt*, vol. 17, no. 12, p. 126017.

Feature extraction using a combination of one or more of LSCI, spectroscopic, and fluorescence images. This processing method may include:

vessel segmentation using intensity-based thresholds, ridge detection, or ridge tracking algorithms;

extracting vessel centerlines using morphological operations on the segmented vessels;

diameter estimation using edge detection techniques, or ridge detection techniques, as described for brain/meningeal vasculature in Li N, Jia X, Murari K, Parlapalli R, Rege A, Thakor N V (2009) "High spatiotemporal resolution imaging of the neurovascular response to electrical stimulation of rat peripheral trigeminal nerve as revealed by in vivo temporal laser speckle contrast," *J Neurosci Meth*, vol. 176, pp. 230-6;

distinguishing between arteries and veins using a combination of spectroscopic images (in which arteries and veins have different light absorption properties) and LSCI images (in which arteries and veins have different blood velocities).

Any of the processing methodologies disclosed in prior art Rege A, Li N, Murari K, Thakor N V (2011) "Multimodal laser speckle imaging of vasculature", International Patent Publication No. WO 2011/029086A2 and Rege A, Senarathna J, Thakor N V (2012) "Anisotropic processing of laser speckle images", International Patent Publication No. WO 2013/049123A1.

Registration of the acquired images to one another. The said registration may be done for multiple images of the same ROI, as is implemented in Miao P, Rege A, Li N, Thakor N V, Tong S (2010) "High resolution cerebral blood flow imaging by registered laser speckle contrast analysis," *IEEE Trans Biomed Engr*, vol. 57, pp. 1152-1157 for mitigating the effect of motion artifact on LSCI; or for images of adjacent ROIs to build a mosaic or panoramic view of a larger ROI. Registration of acquired images to one another may be achieved prior to laser speckle contrast calculation, though an intermittent calculation of speckle contrast may facilitate the identification of features useful for registration, as described in Miao P, Rege A, Li N, Thakor N V, Tong S (2010) "High resolution cerebral blood flow imaging by registered laser speckle contrast analysis," *IEEE Trans Biomed Engr*, vol. 57, pp. 1152-1157.

Spectroscopic imaging. This processing method includes combining images obtained under different illumination either pixel-wise or feature-wise using a combination of mathematical functions (e.g., addition, subtraction, scalar multiplication, and power functions). Images may be normalized based on mean or a certain percentile of intensity values within the image or image stack, before the processing is done.

Figure 2:
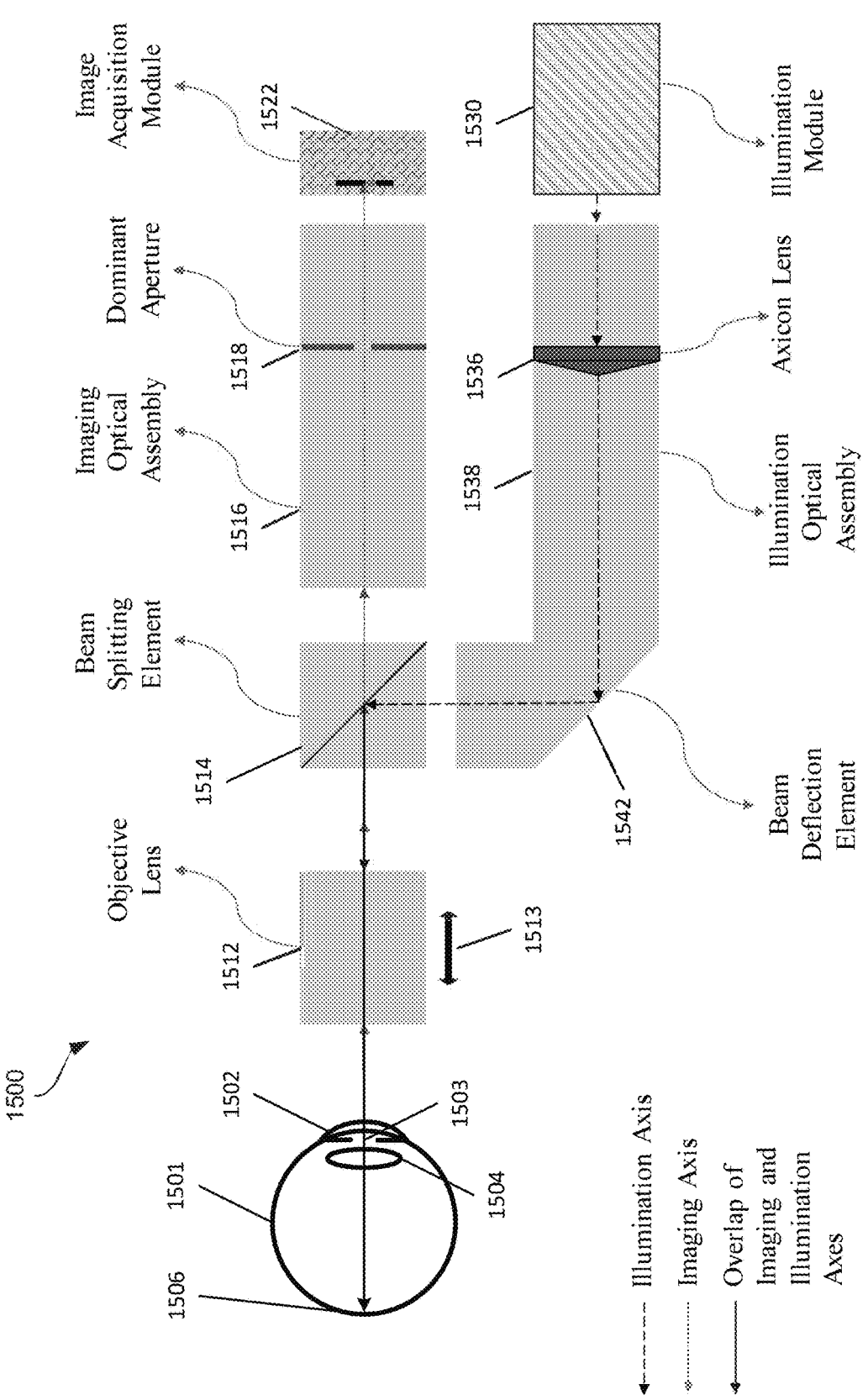
FIG. 2 illustrates light paths from a coherent light source of an OID to a fundus of an eye, according to a first example implementation of an OID system configured for off-axis illumination of an eye.

FIG. 2 illustrates light paths from an illumination module 1530 of an OID 1500 to a fundus 1506 of an eye 1501, and from the fundus 1506 to and image acquisition module 1522, according to a first example implementation. The illumination module 1530 can emit a beam of coherent light. The illumination module 1530 may include optics for transforming coherent light from a light source of the illumination module 1530 into a divergent beam, and additional optics to transform the divergent beam into a collimated beam. An axicon lens 1536 can receive the beam of light from the illumination module 1530 and transform it into a beam that can be focused into an annular cross section. The axicon lens 1536 can be a simple lens, a compound lens, or a lens assembly. In some implementations, the axicon lens 1536 can be an assembly of an odd number of simple lenses. An illumination optical assembly 1538 can receive the beam from the axicon lens 1536 and transform it such that it defocusses to a substantially uniform cross section at an appropriate image plane. The illumination optical assembly 1538 can include one or more simple or compound lenses, one or more lens assemblies, or any combination thereof. In some implementations, the illumination optical assembly 1538 can include other optical components such as a mirror, prism, polarizer, filter, and/or aperture. An "image plane" as used herein refers to one or more planar regions, either within or outside of the OID 1500, where various beams of light come into the desired focal state. For example, at a given image plane, it may be desired to have speckling from the fundus 1506 and/or a gaze fixation target image come into sharp focus, while at the same image plane it may be desired to have coherent or incoherent light defocused such that they have a uniform or substantially uniform distribution of light intensity over a cross section of a region of interest. A first image plane my lie on the fundus 1506 and a second image plane may lie on a light-detecting surface of the image acquisition module 1522. Additional image planes may exist at intermediate points within the OID 1500; for example, between the beam splitting element 1514 and an objective lens 1512.

In some implementations, the OID 1500 can include a reflective surface such as a beam deflection element 1542 to bend the path of light for efficient utilization of space for layout of the optical components. In some implementations, the beam deflection element 1542 can be a mirror or prism. In some implementations, the beam deflection element 1542 can include beam splitting optics, such as a beam splitter or mirror that can facilitate use of a second illumination modality such as an incoherent light source. An example implementation of an OID including a second light source is described below with reference to FIG. 5. The beam deflection element 1542 can receive the light from an illumination optical assembly 1538. The beam deflection element 1542 can direct the light towards a beam splitting element 1514. The light path between the illumination module 1530 and the beam splitting element 1514 can generally be referred to as the illumination light path. There may be multiple beam deflection elements.

The beam splitting element 1514 can direct the illumination beam towards the eye 1501 through the objective lens 1512. In some implementations, the beam splitting element 1514 can be a non-polarizing beam splitter or a polarizing beam splitter. Use of a polarizing beam splitter will reduce the amount of light back-reflected from optical surfaces in the path of light from the beam splitting element 1514 itself to the back of the eye, from reaching the image acquisition module. However, if other polarizers are used in the system to achieve an equivalent result, it may suffice or help to use a non-polarizing beam splitter. In some implementations, the beam splitting element 1514 can be a mirror with a hole in it. In mirror implementations, the coherent light beam can be shaped to be substantially annular around the hole; thus, the mirror will reflect the coherent light beam towards the objective lens 1512. Image light returning from the eye 1501 can be focused such that a pupil 1503 of the eye 1501 is brought into focus at the hole or near it; thus light passing through the pupil 1503 will also pass through the hole in the mirror, and on to the image acquisition module 1522. In some implementations, the hole in the mirror could serve as the dominant aperture stop of the system. The function of the dominant aperture is described further below. The beam splitting element 1514 may also split the beam based on wavelength, that is, reflect light with wavelengths in a specific range of wavelengths while transmitting light with wavelengths in a different specific range of wavelengths. Such an arrangement will have limited utility in implementing laser speckle contrast imaging because light to and from the eye has substantially the same wavelength, but will offer benefits in other applications, such as fluorescence imaging, where emission wavelength is different than the absorption wavelength.

The objective lens 1512 can be a lens, compound lens, or lens assembly. The objective lens 1512 can transform the illumination beam such that the illumination beam comes into focus in the shape of an annulus on or near a cornea 1502 of the eye 1501 before defocusing into a substantially uniform cross section over a region of interest at or near the fundus 1506. The objective lens 1512 can also receive scattered or fluorescent light from the fundus 1506 and pass it back to the beam splitting element 1514. The light path between the beam splitting element 1514 and the region of interest (here, the fundus 1506) can generally be referred to as the combined light path, since both illumination light and scattered light travel along this path, albeit in opposite directions.

Figure 3A:
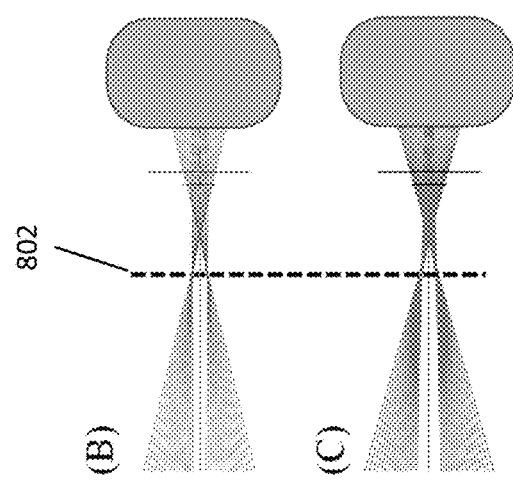
FIG. 3A illustrates a coherent light beam exiting the objective lens of an OID of any of the preceding embodi-ments, according to an example implementation.
Figure 3A:
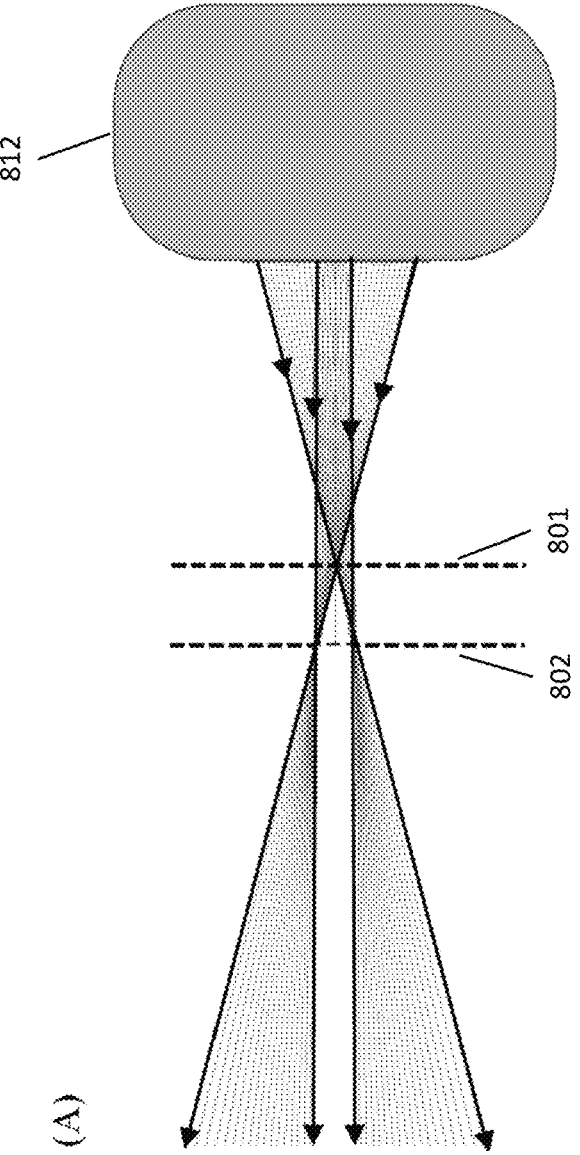
Figure 3B:
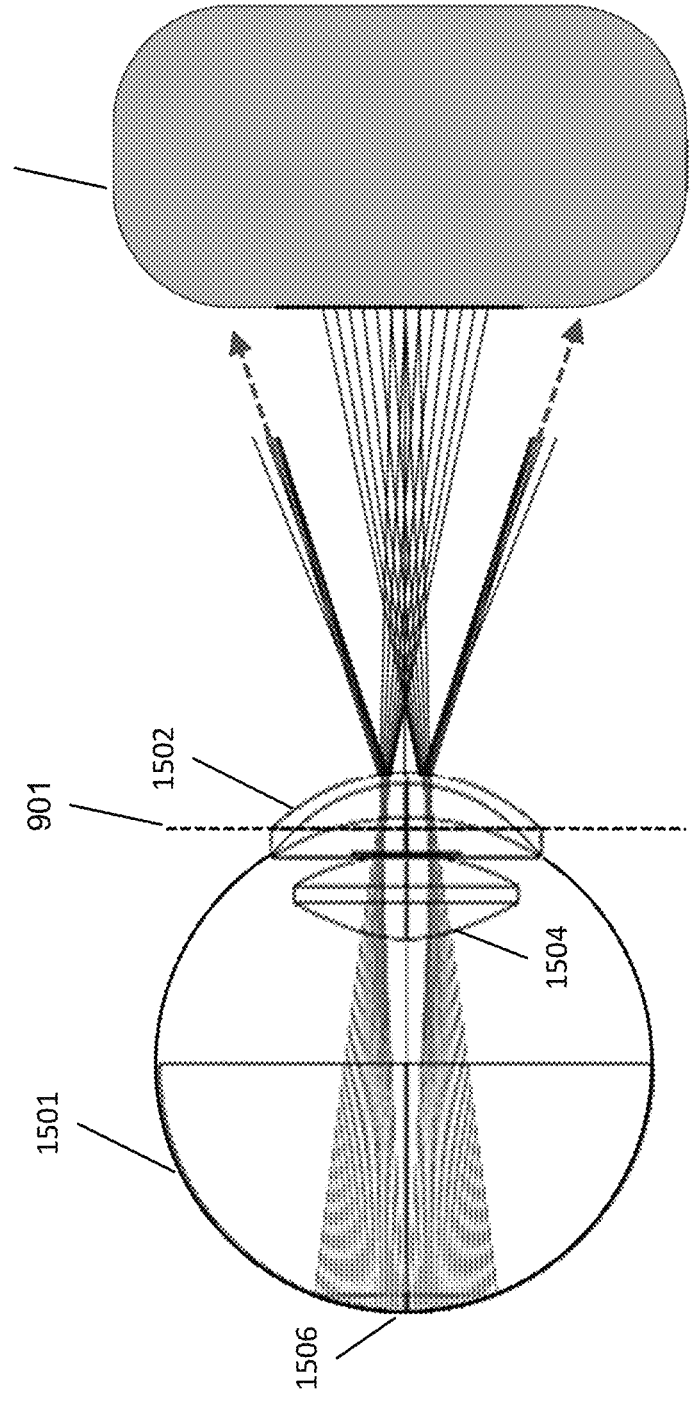
FIG. 3B illustrates the coherent light exiting the objective lens of the OID, passing through the cornea, and illuminat-ing the fundus, according to an example implementation.

The position of the objective lens 1512 can be adjusted along a direction 1513 substantially parallel to the combined light path. The position of the objective lens 1512 can be adjusted to increase the amount of light entering the eye and/or to increase the intensity and/or uniformity of illumination of the fundus 1506. Roughly speaking, the objective lens 1512 can be adjusted to focus the illumination light in a shape on or near the cornea 1502 and/or lens 1504 such that little or no light hits optical surfaces of the eye 1501 on axis in a direction normal to the surfaces. This avoids reflections of light directly back into the imaging optics of the OID 1500. FIGS. 3A and 3B show results of simulations of coherent light striking the cornea 1502 and fundus 1506, respectively, of the eye 1501. The objective lens 1512, in conjunction with the imaging optical assembly 1516, can additionally bring the image light into focus on the image acquisition module 1522. Careful arrangement of the illumination optical assembly 1538 and an imaging optical assembly 1516 can allow the objective lens 1512 to simultaneously focus both illumination light and image light while in the same position such that only the objective lens 1512 need be moved to adjust for, for example, refractive differences in different eyes. The imaging optical assembly 1516 can include one or more simple or compound lenses, one or more lens assemblies, or any combination thereof. In some implementations, the illumination optical assembly 1516 can include other optical components such as a mirror, prism, polarizer, filter, and/or aperture.

The beam splitting element 1514 can direct the scattered light through an imaging optical assembly 1516, which can include an aperture 1518, and ultimately to the image acquisition module 1522. With the aperture 1518 acting as the dominant aperture, neither a diameter of the pupil of the eye nor any other apertures or optics of the system will affect images and measurements taken, for example, using LSCI. To prevent the aperture 1518 from blocking off significant amount of the imaging field of view or the amount of light returning from the fundus 1506, it is useful to include the aperture 1518 at a location in close proximity to the image of a pupil 1503 of the eye 1501 generated by the portion of the imaging optical assembly that lies between the pupil 1503 and the aperture 1518. The aperture 1518 may be of various configurations and dimensions suitable for producing speckles of the appropriate size relative to the pixel size of the image acquisition module 1522. For example, the aperture 1518 may be a pinhole aperture, slit aperture, or circular apertures, and may be of various sizes for finer control of illumination. The aperture 1518 may be fixed or adjustable, much like the filters described previously. Accordingly, in some embodiments, the OID 1500 can include lens and aperture arrangements that to achieve a magnification that enables the formation of an image of the design field of view of the retina on the image acquisition sensor, and achieves a speckle size of approximately twice the pixel size. Speckle size, in this context, is represented by the diameter of the Airy Disc pattern that is produced. Because camera sensors are available or can be produced in diverse sizes, optical magnification of the image formation apparatus of the OID (that is, all elements of the OID that lie between the target eye and the image acquisition sensor) can be configured for effective spatial utilization of the camera sensor area for imaging the desired field of view. Said configuration and magnification may be fixed for the OID or be adjustable.

The above calculations for increasing the FOV without pupil dilation are explained on the basis of the geometry of an average healthy human adult, but the same can be achieved for varying eye sizes and eye conditions and for each type of illumination used in the embodiment. Such an optimization may produce various embodiments each suited for specific cases. For example, an OID system 1400 for imaging the eyes of cats and dogs (i.e., veterinary use) may employ a different embodiment than the embodiment used for imaging human adults. Similarly, an OID system 1400 may employ a different embodiment for imaging infant (premature or otherwise), toddler, pre-pubescent, or adolescent eyes. The OID system 1400 may employ illumination control optics 1410 with adjustable elements that can be tuned for the subject and application prior to imaging. In one embodiment, an opaque eye covering unit can be used to prevent ambient light from reaching the subject's eye so as to cause natural pupil dilation, improving the FOV illuminated and imaged.

The image acquisition module 1522 can be or include an image sensor or camera module that includes a charge couple device (CCD) or an active-pixel sensor such as a complementary metal oxide semiconductor (CMOS) sensor for acquiring and digitizing image frames. The digitized image frames can be passed to a processor of the OID 1500 or to an external computer for processing and display. The light path between the beam splitting element 1514 and the image acquisition module 1522 can generally be referred to as the imaging light path.

In some implementations, the OID 1500 can include one or more light polarizing elements for reduce the amount of reflected light from reaching the image acquisition module 1522. For example, a first light polarizer could be placed in the optical path of the illumination beam, and a second light polarizer could be placed in the optical path of the image light. The polarizers could be, in some implementations, components of the illumination optical assembly 1538 and the imaging optical assembly 1516, respectively. The first polarizer can be configured to selectively pass light of a narrow range of polarization states. The second polarizer can similarly be configured to selectively pass light of a narrow range of polarization states, but in such a manner as to block any light having roughly the same polarization state as the light passed by the first polarizer. Light scattered by the fundus 1506, however, will not have consistent polarization, and thus the second polarizer will pass much of the scattered light on to the downstream optical elements and eventually to the image acquisition module 1522. The second polarizer will block light having the same polarization as passed by the first polarizer, however.

FIG. 3A illustrates a coherent light beam exiting the objective lens 812 of an OID of any of the preceding embodiments, according to an example implementation. After exiting the objective lens 812, the coherent light beam contracts to a beam waist at a first plane 801. As the coherent light beam progresses, it achieves a substantially annular focus at a second plane 802. During an examination, the second plane 802 will be aligned at or near the cornea of the patient. The "dark" region in the middle of the annulus will fall on a portion of the cornea near, and with a surface normal to, an optical axis of the coherent light beam. Because there is little light within this dark region, the cornea and lens will reflect little light back towards the OID along the optical axis. When reduced to practice, the plane of the beam waist 801 and the plane of substantially annular focus 802 may lie in close proximity to each other, almost indistinguishable to the human eye, depending on the diameter of the annulus.

In an eye without refractive errors or accommodation (normal eye), such as in the example (A), the diameter of the dark region within the annulus remains substantially the same beyond the annular focus at the second plane 802. Therefore, in an eye that is not accommodated and focused at infinity (that is, on an object very far away), the inner diameter of the beam will decrease inside the eye and just about reduce to a point leading to substantially uniform illumination at the retina. Example (B) shows an example coherent light beam entering an eye that is hyperopic. Consequently, the diameter of the dark region of the center of the annulus decreases as the coherent light beam progresses past the second plane 802 and the cornea and lens of the eye. This allows for the hyperopic eye which has lesser converging power than a normal eye to achieve substantially uniform illumination at the retina. Example (C) shows an example coherent light beam entering an eye that is myopic or accommodated. This this case, the diameter of the dark region of the center of the annulus increases as the coherent light beam progresses past the second plane 802 and the cornea and lens of the eye. This allows for the myopic or accommodated eye which has greater converging power than a normal eye to achieve substantially uniform illumination at the retina.

FIG. 3B illustrates a coherent light beam exiting the objective lens 912 of an OID of any of the preceding embodiments and entering an eye 1501, according to an example implementation. A coherent light beam of illumination light exits the objective lens 912 and contracts to a beam waist, and then to an annular cross section at a plane 901. The plane 901 can be aligned at or near a leading surface of a cornea 1502 or lens 1504. The annular cross section has a "dark" region in the center at and around an optical axis (imaging axis). Because little if any light strikes the surfaces of the cornea 1502 or lens 1504 at or near the optical axis, any reflections from the cornea 1502 or lens 1504 diverge away from the optical axis. Thus, the reflected light either does not re-enter the objective lens 912 of the OID, or absorbed, blocked, or otherwise rejected by apertures within the OID. Coherent light that does enter the eye 1501, however, defocuses as it traverses an interior of the eye to generate a substantially uniform region of illumination on a fundus 1506 of the eye.

Figure 3C:
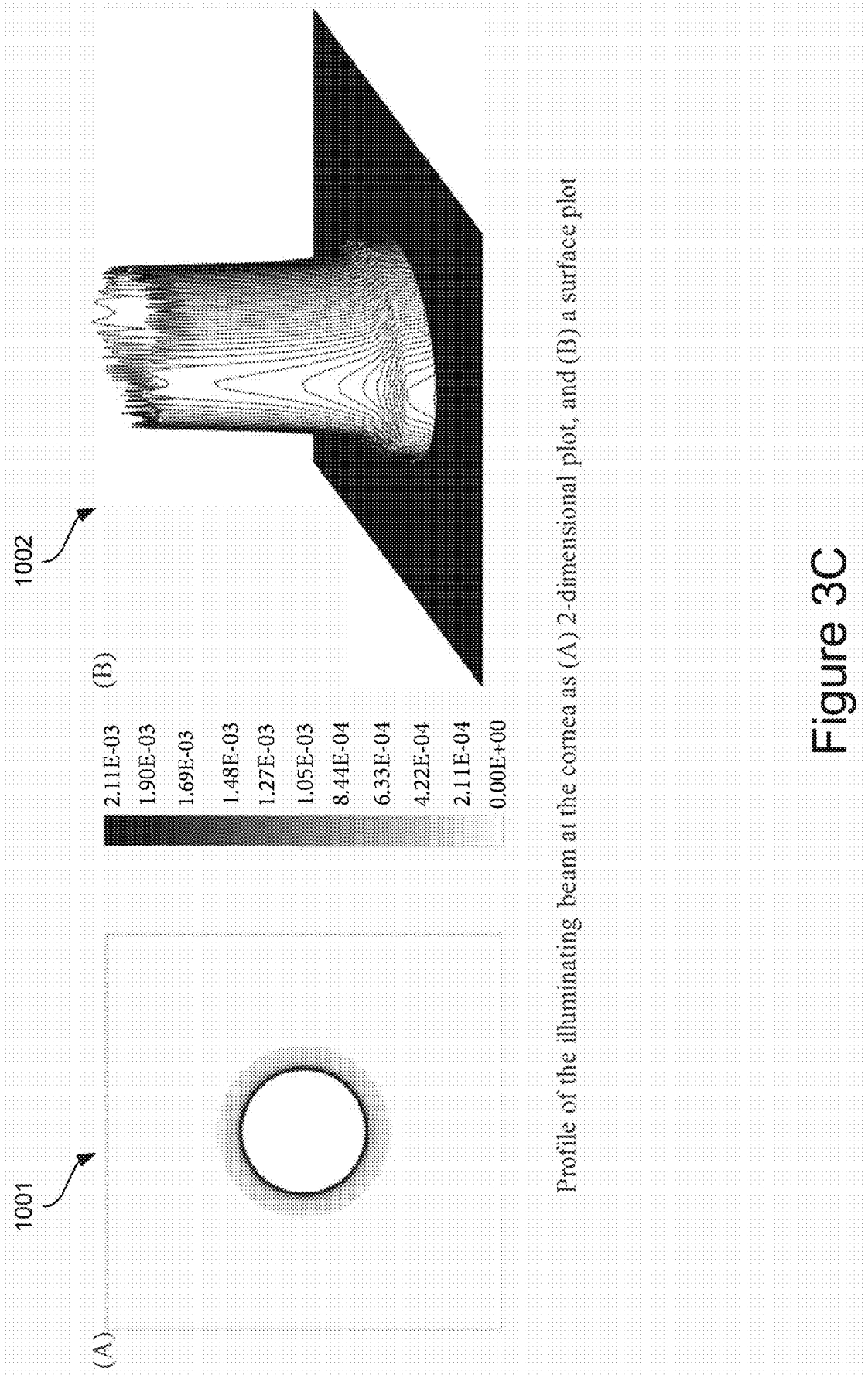
FIG. 3C shows results of a simulation of a coherent light beam from an OID incident on the cornea, according to an example implementation.

FIG. 3C shows results of a simulation of a coherent light beam from an OID incident on the cornea 1502, according to an example implementation. The simulation results include a 2-dimensional plot 1001 and a surface plot 1002. Both the 2-dimensional plot 1001 and the surface plot 1002 show a roughly annular distribution of light incident on the cornea 1502. While some of this light may reflect off the cornea, the surface of the cornea that the annulus of light strikes is not at an angle normal to the path of light, thus few if any reflections will travel back along the optical path to an image acquisition module of the OID.

Figure 3D:
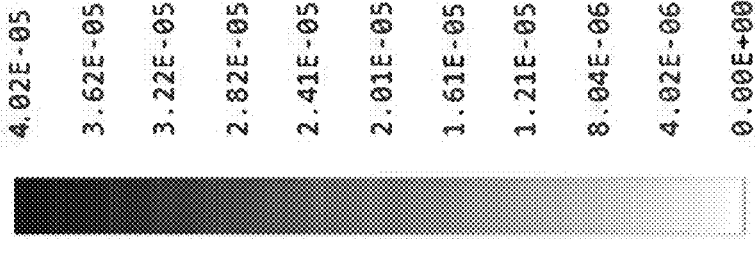
FIG. 3D shows results of a simulation of coherent light from the OID incident on a retina, according to an example implementation.
Figure 3D:
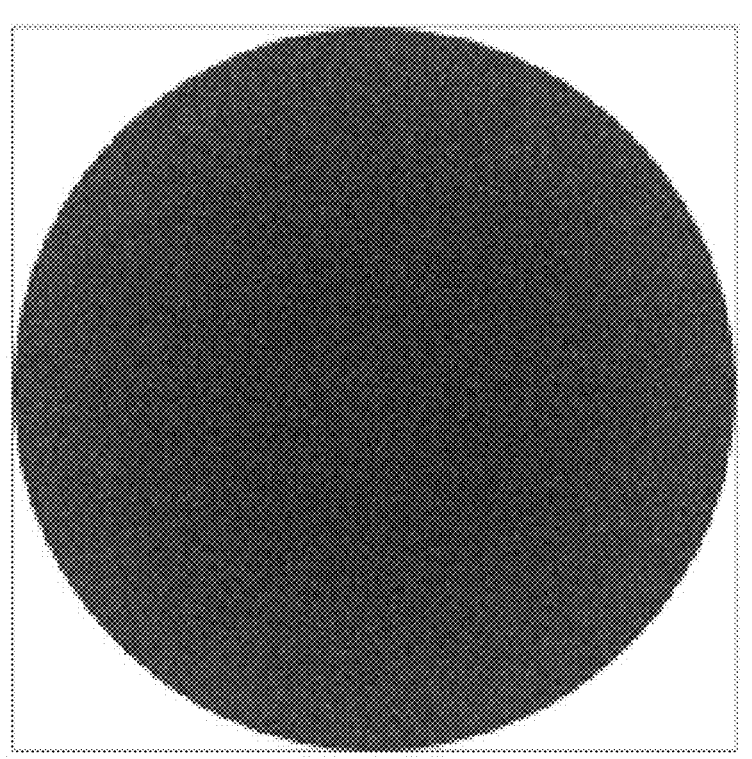

FIG. 3D shows results of a simulation of a coherent light beam from an OID incident on the fundus 1506 of an eye 1501, according to an example implementation. Once the light passes through the cornea 1502 and lens 1504 it diverges again before striking the fundus 1506. When the illumination optics are properly arranged, the light will illuminate the fundus 1506 uniformly or substantially uniformly within a radius. The radius will represent a region that is just larger than the field of view of the device.

In an alternative embodiment, rather than the circular or substantially circular illumination provided by the axicon lens and other optics, a rectangular illumination can be achieved using cylindrical lenses and applying the same principles of off-axis transmission of light into the eye. Cylindrical lens implementations are described below with reference to FIG. 9.

Figure 3E:
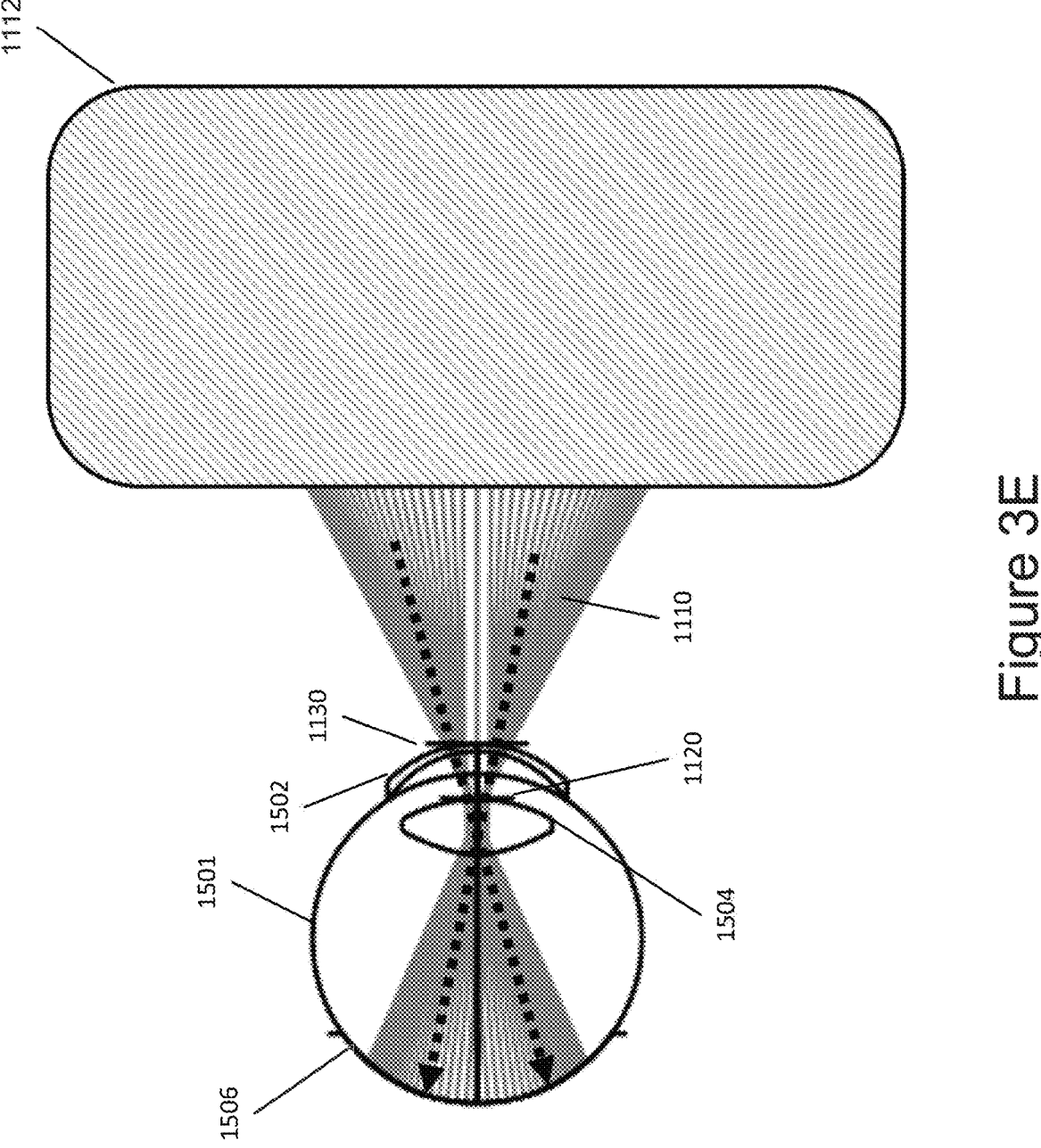
FIG. 3E illustrates another configuration in which the coherent light beam may exit the objective lens of an OID to illuminate a substantially larger field of view.

FIG. 3E shows another embodiment that is configured to illuminate and image a wider field of view of the fundus 1506 than previously described in FIG. 3A and FIG. 3B and in particular, also depicts an illuminating beam 1110 wherein a beam waist 1120 lies beyond (further away from the objective lens 1112 than) a plane of annular focus 1130 and the beam 1110 lacks an inner diameter past the anterior structures (e.g., a cornea 1502 and lens 1504) of the eye 1501. An inner diameter just about forms (limiting case) at the fundus 1506, that is, had light continued to transmit past the fundus 1506, an inner diameter would have formed and increased with distance as the beam 1110 diverges. The OID may be configured to accomplish substantially uniform illumination at the fundus 1506 while avoiding back reflection from the anterior portion of the eye 1501 such as the cornea 1502) in multiple ways. The illuminating beam 1110 may also be configured to compensate for refractive errors or state of accommodation by adjusting the optics to adjust beam characteristics similar to FIG. 3A.

Figure 4:
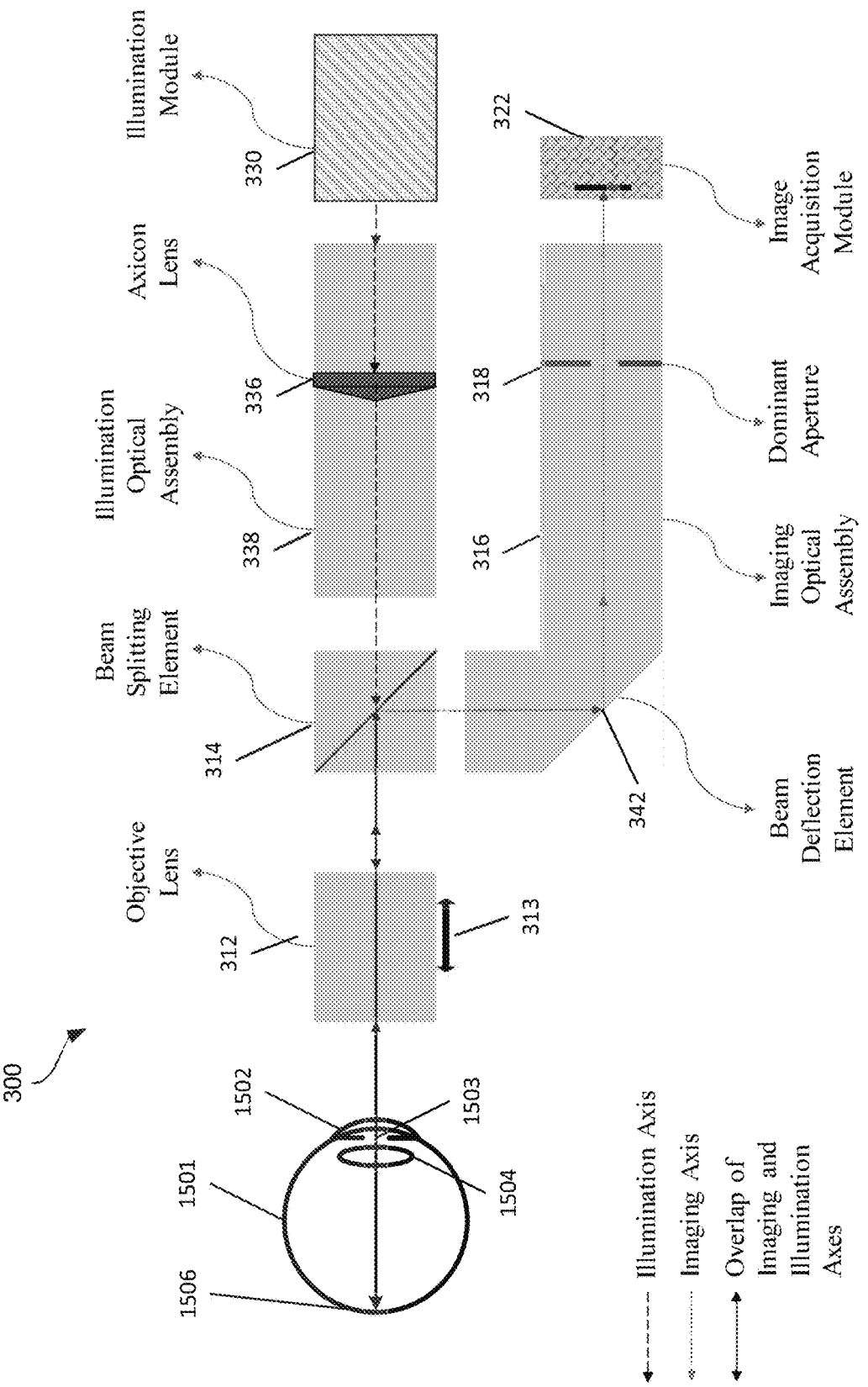
FIG. 4 illustrates light paths from a coherent light source of an OID to a fundus of an eye, according to a second example implementation of an OID system configured for off-axis illumination of an eye.

FIG. 4 illustrates light paths from an illumination module 330 of an OID 300 to a fundus 1506 of an eye 1501, and from the fundus 1506 to and image acquisition module 322, according to a second example implementation. The OID 300 includes components similar to or the same as the OID 1500, but arranged differently. In particular, the OID 300 differs from the OID 1500 in that the OID 1500, the imaging light path and the combined light path substantially share the same optical axis; that is, the image light path and the combined light path are aligned, while the illumination light path is bent. The OID 300, in contrast, has its illumination light path aligned with the combined light path, and a bent imaging light path. In practice, neither path need be "bent" in either configuration. Adding the beam deflection element 1542 and/or 342 to "bend" one of the light paths, however, can allow the OID 300 and/or 1500 to be more compact.

The OID 300, an illumination module provides illumination light, which passes through the axicon lens 336, the illumination optical assembly 338, and to the beam splitting element 314. The beam splitting element 314 can pass the illumination light to an objective lens 312, which, via positional adjustment along a direction 313, can focus the illumination light on or near the cornea 1502 and/or lens 1504. The objective lens 312 can receive the image light from the fundus 1506 and pass it to the beam splitting element 314, which can direct the image light towards a beam deflection element 342. The beam deflection element 342 can direct the image light through imaging optical assembly 316, an aperture 318, and to the image acquisition module 322.

Figure 5:
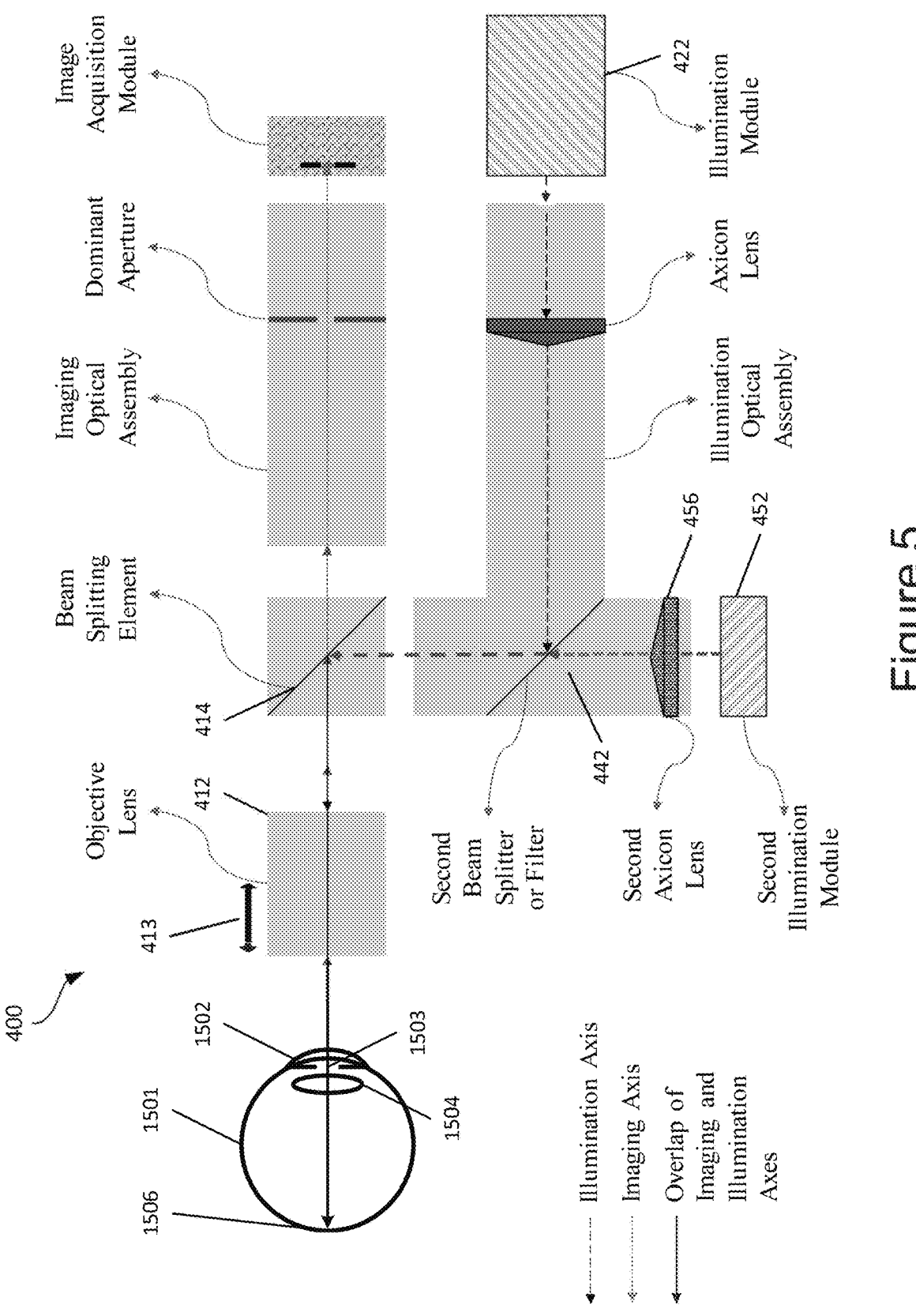
FIG. 5 illustrates an OID with an incoherent light source, according to an example implementation.

FIG. 5 illustrates an OID 400 with an added incoherent light source, according to an example implementation. The arrangement of the optics in the OID 400 can provide for illumination of a fundus that coincides at least in part with the coherent illumination provided by a coherent light source in an illumination module 422. In the OID 400, a beam deflection element in the "bent" path of the device can be replaced or supplemented by a second beam splitting element 442 such as a beam splitter or filter. A second illumination module 452 can produce incoherent light and direct it towards a second axicon lens 456, which can transform the incoherent light beam such that it focuses into a substantially annular shape before defocusing into a substantially uniform cross section at one or more image planes. The second illumination module 452 can include incoherent light source such as a lamp, bulb, LED or any other light-emitting device. In some implementations, the second axicon lens 456 can be replaced with an obstacle placed in the middle of the incoherent light beam, such that a portion of the incoherent light beam at and surrounding the optical axis is blocked. When the image of the obstacle is focused on or near the cornea 1502 and/or lens 1504, the image of the obstacle can again fall on the optical axis, thus reducing or eliminating any light striking the cornea 1502 or lens 1504 on axis and at an angle normal to their surfaces. Having passed through the second axicon lens 456 or obstacle, the incoherent light beam enters the second beam splitting element 442, which can direct the incoherent light beam to a first beam splitting element 414. The first beam splitting element 414 can direct the incoherent light beam through the objective lens 412, which, via positional adjustment along a direction 413, can focus the beam into the substantially annular shape on or near the cornea 1502 and/or lens 1504. Within the eye 1501, the incoherent light will naturally diffuse and illuminate the fundus 1506 substantially uniformly. The return path for scattered and reflected light is the same as that for the coherent light and as described with reference to FIG. 2 described previously.

Figure 6:
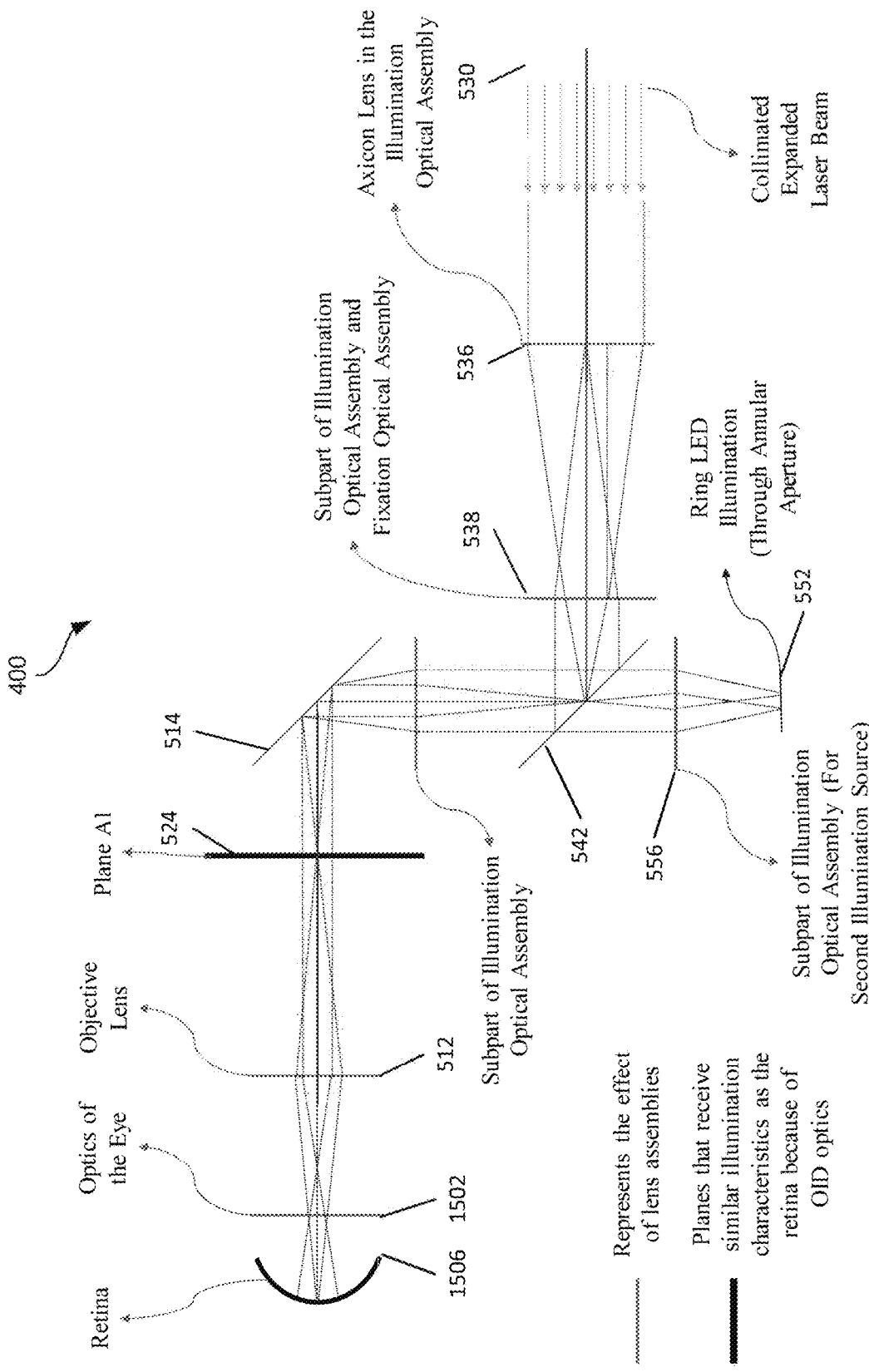
FIG. 6 illustrates light paths in the OID 400 of FIG. 4, according to an example implementation.

FIG. 6 illustrates light paths in the OID 400 of FIG. 5, according to an example implementation. The narrow solid lines represent lens assemblies and their effects on light beams. The broad solid lines represent planes that, due to the configuration of the OID optics, receive similar illumination characteristics as the fundus 1506. The dashed lines represent the light beam. FIG. 6 is meant to be representational only, and is not necessarily drawn to perfect scale. The dashed lines generally illustrate the expected behavior of the illumination light beam through the various components of the system, but are not intended to be exact or limiting within the context of this disclosure.

An illumination module 530 generates a laser beam. In the example implementation shown in FIG. 6, the illumination module 530 can generate a collimated expanded laser beam.

The collimated expanded laser beam travels through an axicon lens assembly 536, which transforms the beam into one that can focus into a substantially annular shape. The illumination light beam travels through an illumination optical assembly 538, a first beam splitting element 542, a second beam splitting element 514, an objective lens 512, and comes into focus in a substantially annular shape at or near the cornea 1502. The illumination light beam defocuses as it passes through the optics and interior of the eye, and forms a substantially uniform illumination on the fundus 1506.

The OID 400 may also include a second light source, which in this example is an incoherent light source. In this example, the second illumination module 552 is a ring LED emitting incoherent light through an annular aperture. Because of low coherence and the ability of the LED illumination to diffuse, an axicon or cylindrical lens may not be needed to achieve off-center illumination. An annular aperture produces an equivalent effect, especially if the annular aperture can be focused on the anterior section of the eye. The incoherent light beam travels through a second optical assembly 556 and to the first beam splitting element 542, which combines the incoherent light beam with the coherent light beam from the illumination module 530. The incoherent light beam, following a similar path as the coherent light beam, passes through the second beam splitting element 514 and the objective lens 512 before coming into focus at or near the cornea 1502 in approximately the same shape as the annular aperture of the second illumination module 552. The incoherent light beam then defocuses and diffuses as it passes through the optics and interior of the eye, and forms a substantially uniform illumination on the fundus 1506.

The OID 400 is configured such that both the coherent light beam and the incoherent light beam defocus and/or diffuse such that they illuminate a region of interest of the fundus 1506 substantially uniformly. Because both beams travel through the objective lens 512, it is advantageous to configure the OID 400 such that adjustment of the objective lens 512 results in both beams achieving the desired shape and cross section at the same image plane. Thus, the illumination optical assembly 538 and the second optical assembly 556 can both be configured to achieve the desired shape and cross section as they pass through Plane A1 524. The objective lens 512 can then be adjusted to repeat the same or similar cross section at the fundus 1506.

Figure 7:
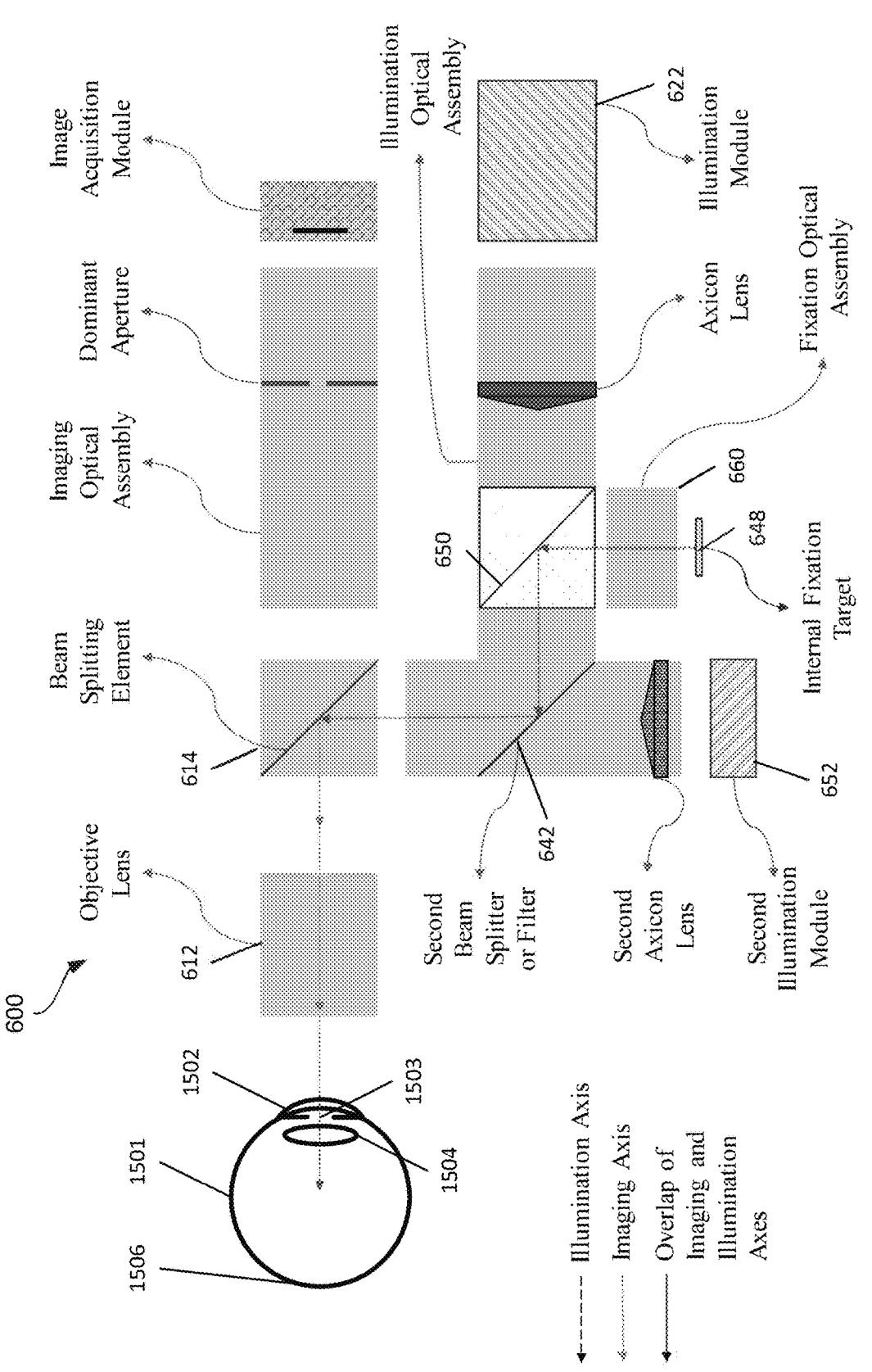
FIG. 7 illustrates an OID with an internal gaze fixation target for holding a patient's gaze steady during imaging, according to an example implementation.

FIG. 7 illustrates an OID 600 with an internal gaze fixation target 648 for holding a patient's gaze steady during imaging, according to an example implementation. The internal gaze fixation target 648 can appear as a light or shape in the patient's field of vision. The target 648 may be back lit, front lit, or may simply be light source itself such as an LED or small lamp. In some implementations, the target 648 may include an aperture to set the size or shape of the visible target. The patient can avoid large movements of his or her eye during imaging by focusing on the target 648, which can have a steady position relative to the illumination and imaging optics of the OID 600. The internal gaze fixation target 648 can include an illuminated point or shape. The target 648 may have a fixed position within the OID 600, or moveable to allow the operator of the OID 600 to direct the patient's gaze in a desired direction. The target 648 can be turned on or off depending on the needs of a particular imaging operation. In some implementations, the OID 600 can include in addition or alternatively to the internal gaze fixation target 648, an external gaze fixation target. An external gaze fixation target may include a light, pointer, or other shape visible to the non-imaged eye. By tracking the external gaze fixation target with the contralateral eye, the patient may steady the position of the imaged eye as well. The target 648 introduces a target light beam into the internal optics of the OID 600, which can combine the target light beam with one or more illumination light beams and/or aligned with the image light beam.

The internal gaze fixation target 648 emits the target light beam towards a first beam splitting element 650, which can combine the target light beam with a coherent light beam from a first illumination module 622. The first beam splitting element 650 can direct the target light beam and the coherent light beam towards a second beam splitting element 642, which can combine the beams with an incoherent light beam from the second illumination module 652. The second beam splitting element 642 can direct the beams toward a third beam splitting element 614, which can direct the beams towards an objective lens 612, and on to the eye 1501. The optical path of the target light beam can pass through a fixation optical assembly 660, which can transform the target light beam such that the target comes into focus for the patient in the appropriate plane relative to the illumination light beams. In particular, the target 648 can come into focus where, for example, the coherent illumination beam is defocused such that when the coherent light beam provides substantially uniform illumination across a field of view of the fundus 1506, the target 648 can come into sharp focus on the fundus 1506. As both the illumination light beams and the target light beam pass through the objective lens 612, the fixation optical assembly 660 can be configured such that the illumination light beams achieve a substantially uniform cross section in the same plane in which the target light beam comes into sharp focus. This plane can be an image plane internal to the OID 600, as described further below with reference to FIG. 8. Thus, adjusting the objective lens 612 should adjust the location of this image plane simultaneously for both the illumination light beams and the target light beam.

Figure 8:
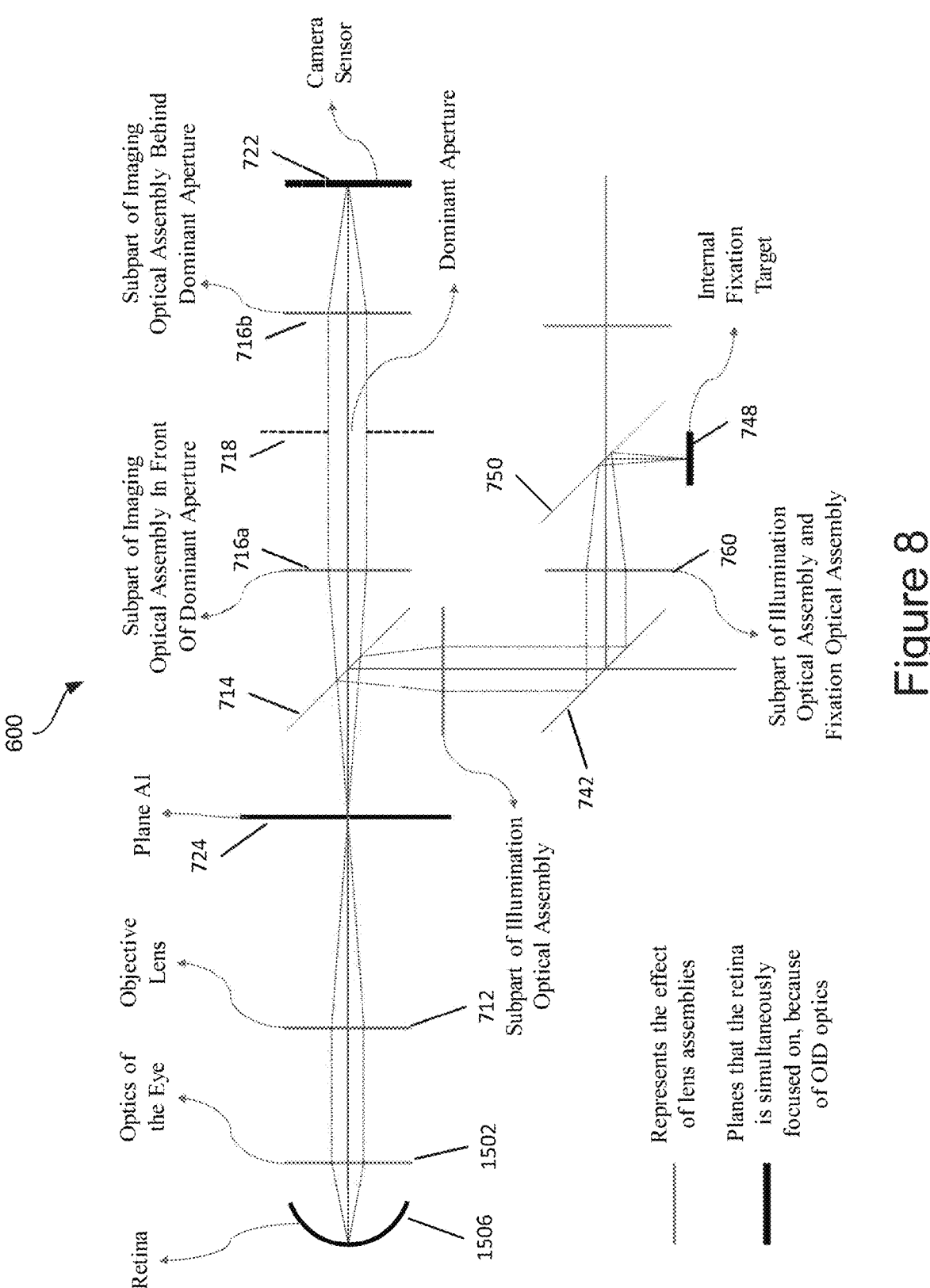
FIG. 8 illustrates light paths in an OID with a gaze fixation target for use in fixating a patient's eye and lens during imaging, according to an example implementation.

FIG. 8 illustrates light paths in the OID 600 of FIG. 7, according to an example implementation. An internal gaze fixation target 748 emits a target light beam towards a first beam splitting element 750. The first beam splitting element 750 can direct the target light beam through a first optical assembly 760 and to a second beam splitting element 742. The first and second beam splitting elements 750 and 742 can combine the target light beam with one or more illumination beams, such as a coherent light beam and an incoherent light beam. The second beam splitting element 742 can direct the target light beam towards a third beam splitting element 714. The third beam splitting element 714 can direct the target light beam towards an objective lens 712. Between the third beam splitting element 714 and the objective lens 712 lies an image plane 724. The various optical assemblies of the illumination and target light paths are configured such that the target light beam and the illumination light beam achieve a desired focus (or defocused state) at the image plane 724. This state can correspond to the state of the light beams when they strike the fundus 1506. For the illumination light beams, this may be a substantially uniform distribution of light energy across a region of interest. For the target light beam, the target image may be brought into sharp focus. Similarly, the image plane 724 will also represent the focus of an image light beam returning from the fundus 1506. The image light beam can consist of light reflected, scattered, or emitted from the fundus 1506. This point of focus of the image light will also correspond to the focus of the image light at the camera module 722 (which is positioned at a second image plane). A position of the objective lens 712 can be adjusted to compensate for refractive differences in the optics of the eye 1501 (i.e., lens 1504 and/or cornea 1502), as well as to variations in distance from the OID 600 to the eye. The adjustment to the objective lens 712 can bring all of the various light beams—the illumination light beams, the target light beams, and the image light beams—into the desired focus simultaneously, reducing the number of separate adjustments necessary during and between examinations.

The image light beam returning from the fundus 1506 travels back through the lens 1504 of the eye 1501, the objective lens 712, and to the third beam splitting element 714. The third beam splitting element directs the image light beam through imaging optics 716a and 716b and an aperture 718, which acts as a dominant aperture stop of the imaging optical path. The image light beam can be brought into focus at the camera module 722.

Figure 9:
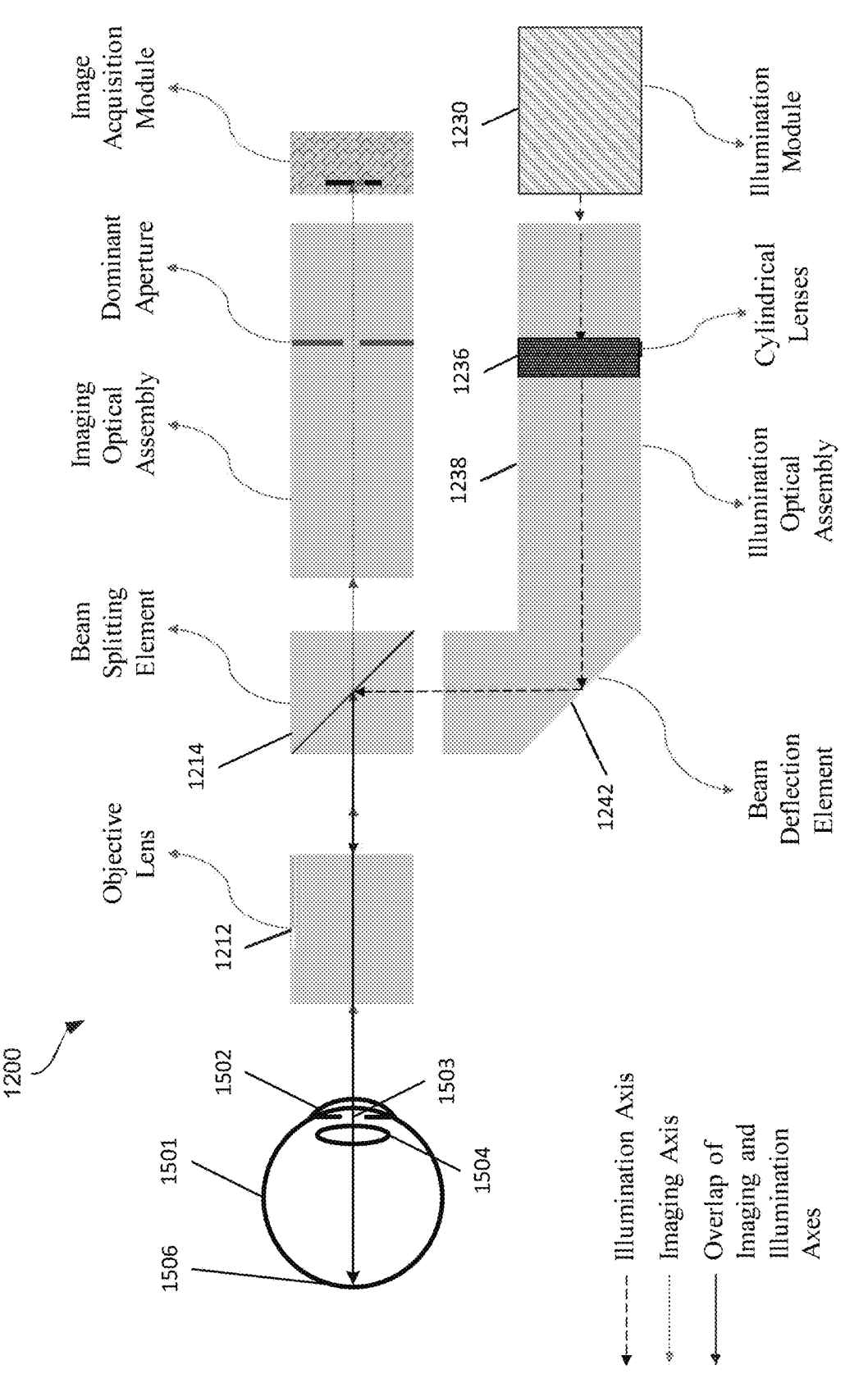
FIG. 9 illustrates light paths from a coherent light source of an OID, through cylindrical lenses to a fundus of an eye, according to an example implementation of an OID system configured for off-axis illumination of an eye.

FIG. 9 illustrates light paths from a coherent light source of an OID 1200, through cylindrical lenses 1236 to a fundus 1506 of an eye 1501, according to an example implementation of an OID system configured for off-axis illumination of an eye. The OID 1200 is similar to the OID 1500, and may share many components in common. However, rather than employing an axicon lens to generate a coherent light beam with an annular focus, the OID 1200 includes one or more cylindrical lenses 1236 for generating a coherent light beam that can focus into one or more substantially rectangular shapes. In an example implementation, the illumination module 1230 can emit a beam of coherent light towards the cylindrical lenses 1236. The cylindrical lenses 1236 need not be perfectly cylindrical in shape; rather, "cylindrical" simply refers to a profile that curves along a first axis orthogonal to the optical axis (where the optical axis is parallel to a direction of the coherent light beam), but that is substantially flat along a second axis orthogonal to both the first axis and the optical axis. In some implementations, there can be two cylindrical lenses 1236, which can transform the coherent light beam such that it comes into focus as two substantially line (or thin rectangular) shapes, one on either side of the optical axis. In some implementations, there can be more than two cylindrical lenses 1236, where the plurality of cylindrical lenses 1236 can be configured to transform the coherent light beam such that it comes into focus in polygonal or substantially polygonal shapes distributed around the optical axis.

The coherent light beam can exit the cylindrical lenses 1236 and pass through the illumination optical assembly 1238, deflect off a beam deflection element 1242, pass through and/or deflect off of a beam splitting element 1214, pass through an objective lens 1212, and enter the eye 1501. The objective lens 1212 can bring the coherent light beam into focus as one or more substantially polygonal shapes positioned around the optical axis, at or near a cornea 1502 or lens 1504 of the eye 1501. After passing through the optics of the eye 1501, the coherent light beam can defocus such that it illuminates a region of interest of the fundus 1506 substantially uniformly. For example, in some implementations, the coherent light beam can focus as two substantially rectangular regions at or near the cornea 1502 or lens 1504, but with little or none of the coherent light beam striking the cornea 1502 or lens 1504 at or near the optical axis, and defocus into two adjacent or slightly overlapping rectangular regions on the fundus 1506.

The OID 1200 can include additional light sources; for example, an incoherent light source such as the second illumination module 452 and accompanying optics of the OID 400, or a target light such as the internal gaze fixation target 648 and accompanying optics of the OID 600.

Figure 10:
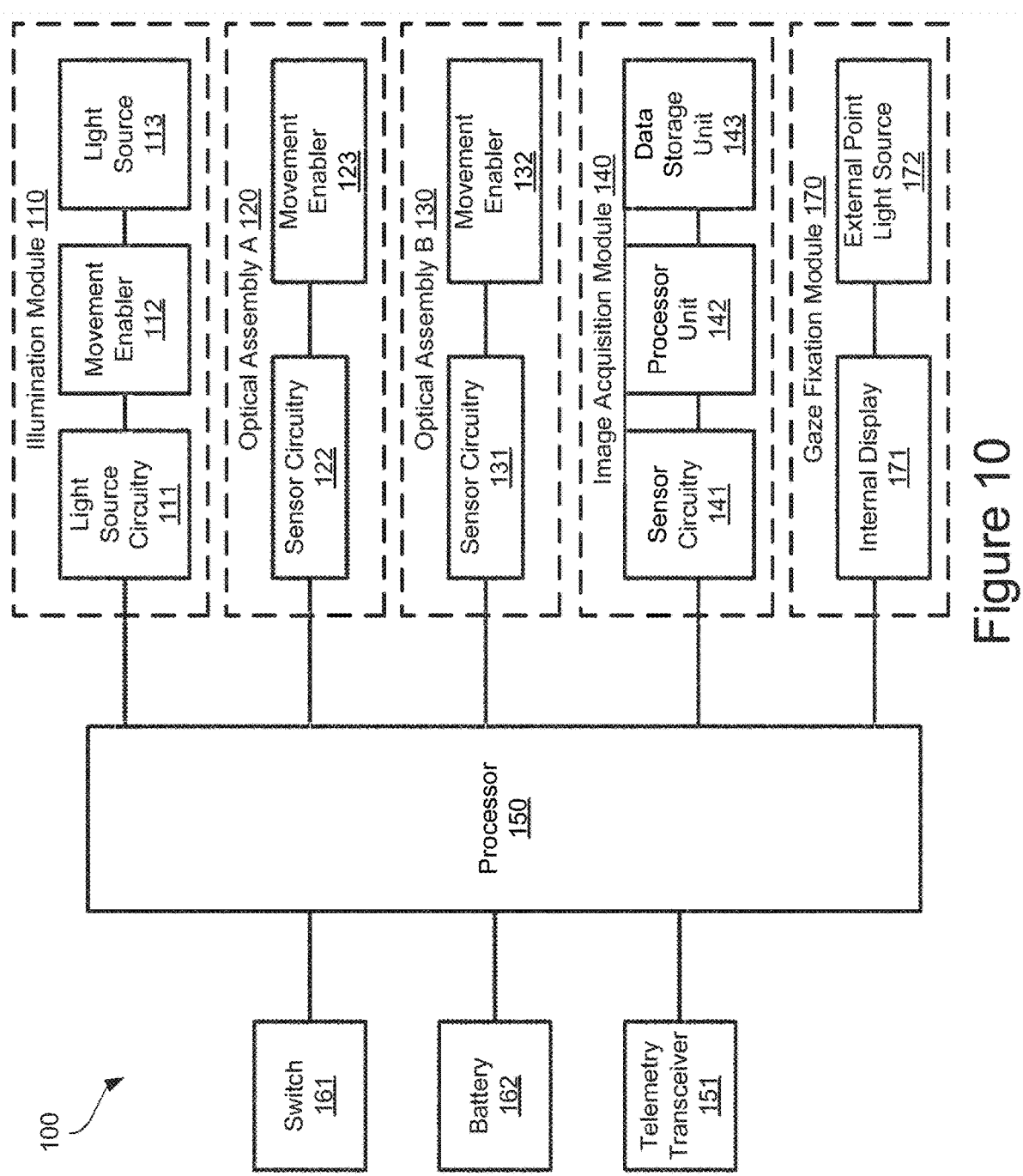
FIG. 10 is a schematic of the electrical components of the OID.

FIG. 10 shows a schematic of the electrical components of an example OID 100. A switch 161 allows the user to activate or deactivate the functionality of the OID 100 while one or more batteries 162 power the electrical components. In some embodiment, the one or more batteries 162 can power some or all of the electrical components of the OID 100. In some embodiments, the one or more batteries 162 may be incorporated within the OID 100, while in other embodiments, one or more of the batteries 162 can be external. Some embodiments may not be battery-powered and instead receive electrical power from other sources such as the mains, a computer such as via the USB port, or other power storage units. A telemetry transceiver 151 allows data to be transmitted to and from the OID 100. In some embodiments, the telemetry transceiver 151 may be replaced by another communication mechanism. A processor unit 150 processes signals from the various electrical components, including the illumination module 110, Optical Assembly A 120 and Optical Assembly B 130, the image acquisition module 140, and the gaze fixation module 170. The illumination module can include a light source circuitry unit 111 and a movement enabler unit 112 to manipulate the light source 113. The Optical Assembly A 120 comprises sensor circuitry 122 and may also include a movement enabler unit 123. The Optical Assembly B 130 comprises sensor circuitry 131 and may also include a movement enabler unit 132. The image acquisition module 140 comprises sensor circuitry 141, a processor unit 142, and a data storage unit 143. A movement enabler could be a stepper motor, other type of motor, servo, gear assembly including rack and pinion, and may be electronically or mechanically controlled. A Movement Enabler may or may not be present in each module. Typical function of the Movement Enabler is selective engagement of specific light source specific optical filters, adjustment of lenses to obtain focus or uniform illumination or to compensate for the characteristics of the imaged eye such as refractive errors. A Movement Enabler may also be used to translate the camera. In some implementations, the OID 100 may include only a single optical assembly or additional optical assemblies. In some implementations, the optical assemblies may share optical or mechanical elements with each other, and/or with the illumination module; for example, in some implementations, an optical assembly and an illumination module may share an objective lens or lens assembly. Sharing the objective lens may facilitate focusing both illumination light and scattered (image) light simultaneously with a single adjustment; for example, by moving the position of the objective lens with respect to an imaging target or other optical elements of the OID 100.

The gaze fixation module 170 can include an internal display 171 and an external point light source 172. In alternative implementations, however, the gaze fixation module 170 could include both internal and external display and/or internal and external point light source. The internal display 171 can include an LCD or LED display suitable for displaying an image such as target shape. Target shapes can include points, crosses, bullseyes, starts, etc. Optics of the OID 100 can present the image to a patient. The patient can keep the gaze of the imaged eye fixated on the target shape as a means of holding their eye steady during imaging. In some implementations, the internal display 171 can, under the control of the processor unit 150, move the target shape around on the display to cause the patient to change the position of her eye as she follows the shape; thus positioning the eye for imaging of different regions of the fundus. The external point light source 172 can be a gaze fixation target for the contralateral eye, since fixing the position of the contralateral eye will result in the patient holding the imaged eye steady as well. The external point light source 172 can include an LED, lamp, or even another computerized display. In some implementations, the external point light source 172 can have a fixed position. In some implementations, the OID can include one or more movement enablers such as servos, motors, or other means for automatic positioning of the external point light source 172. In some implementations, a user of the OID 100 can manually position the external point light source 172.

The control of the various modules of the OID 100 can be achieved using the processor unit 150. Examples of control activity include: invoking one or more illumination sources of the illumination module 110 for an appropriate amount of time, motion of the components of the Optical Assembly A 120 and Optical Assembly B 130 for focusing on appropriate ROI of the target tissue, for example tissue of the eye 1401, control of the gaze fixation apparatus (described previously in this disclosure), recording and basic processing of images under appropriate illumination, invoking the appropriate modality for storage and/or transmission of the images, power management, data management and storage, and invoking advanced analytics on the images. One embodiment will have the processor unit 150 physically located on the OID 100 and could be an FPGA, a microprocessor, or a microcontroller. Another embodiment has the processor unit 150 located remotely and communication to and from the OID 100 will be established via a telemetry transceiver 151, USB, or any other standard or proprietary channels.

Figure 11:
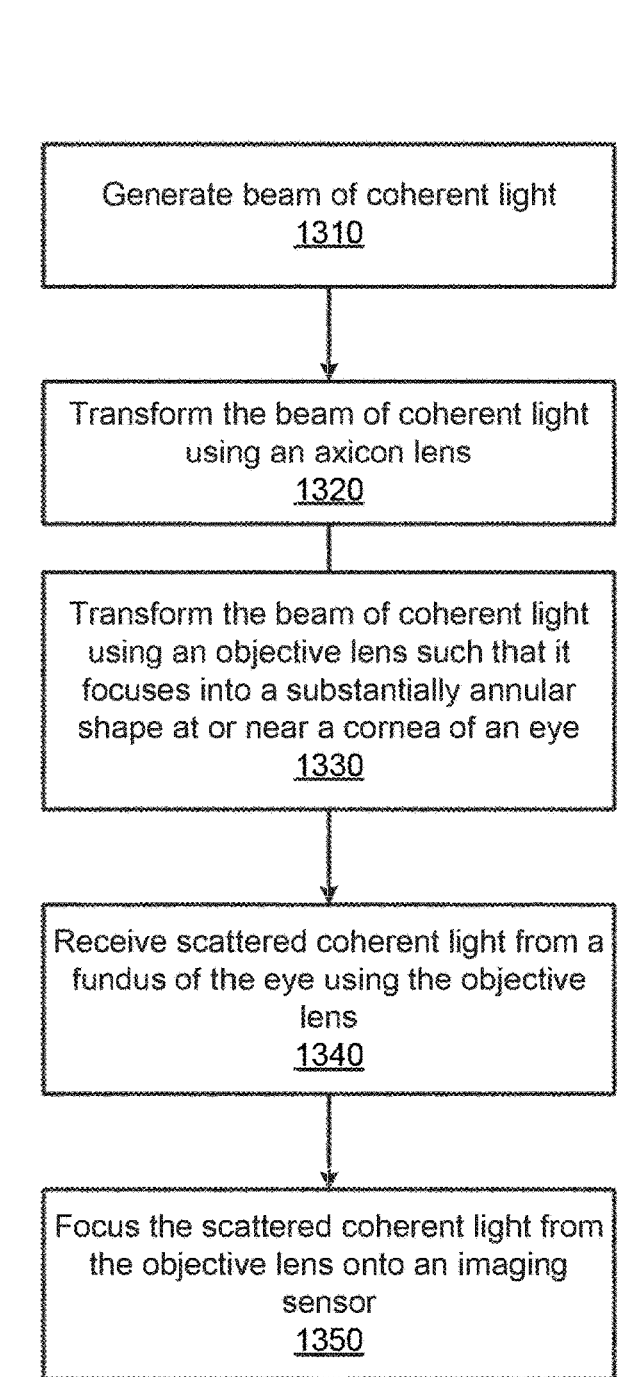
FIG. 11 shows a flowchart illustrating an example method for off-axis illumination of an eye, according to an example implementation.

FIG. 11 shows a flowchart illustrating an example method 1300 for off-center illumination of an eye, according to an example implementation. The method 1300 can be performed using any of the OIDs or OID systems 100, 1400, 1500, 300, 400, 600, and 1200 described herein. The method 1300 includes generating a beam of coherent light (1310), transforming the beam of coherent light using an axicon lens (1320), transforming the beam of coherent light using an objective lens such that it focuses into a substantially annular shape at or near a cornea of an eye (1330), receiving scattered coherent light from a fundus of the eye using the objective lens (1340), and focusing the scattered coherent light from the objective lens onto an imaging sensor (1350).

The method 1300 includes generating a beam of coherent light (1310). The beam of coherent light can be generated by a laser. The beam of coherent light can be in the infrared or near-infrared wavelength range. In some implementations, the beam of coherent light may be in the visible spectrum of light. Generating the beam of coherent light may include using beam-spreading optics to generate a broader beam. Generating the beam of coherent light may additionally include using optics, such as one or more of an aperture, mirror, prism, and/or beam splitting element, to split the beam into two or more beams.

The method 1300 includes transforming the beam of coherent light using an axicon lens (1320). The axicon lens can be a simple lens, a compound lens, or a lens assembly. In some implementations, the axicon lens can be made up of an odd number of lenses. The axicon lens can transform the beam of coherent light such that it focuses into a first substantially annular shape at a first image plane. In alternative implementations, different shaped lenses may be employed to provide off-axis illumination of the eye; for example, cylindrical lenses.

The method 1300 includes transforming the beam of coherent light using an objective lens such that it focuses into a substantially annular shape at or near a cornea of an eye (1330). The objective lens can be a simple lens, a compound lens, or a lens assembly. The objective lens can transform the beam of coherent light using an objective lens such that it focuses into a second substantially annular shape at or near a cornea of an eye before defocusing into a substantially uniform cross section at or near a fundus of the eye. In this manner, as the beam of coherent light passes through the cornea and lens of the eye, little or none of the light strikes the cornea or lens at or near an optical axis. Thus, reflections of light will angle away from the OID and little if any of the light will reflect directly back into the OID. Of what little reflected light enters the OID, most if not all can be rejected by one or more apertures in an imaging optical path of the OID. Light that enters the eye can defocus as it travels across an interior of the eye and illuminate a region of interest of the fundus substantially uniformly. The fundus can scatter the beam of coherent light.

The method 1300 includes receiving scattered coherent light from the fundus using the objective lens (1340). The objective lens can transform the scattered coherent light, and pass it to downstream optics of the imaging optical path. In some implementations, the method 1300 includes passing the scattered light through an aperture configured to act as a dominant aperture stop of an optical path between the fundus and the image sensor.

The method 1300 includes and focusing the scattered coherent light from the objective lens onto an imaging sensor (1350). The imaging sensor can be, for example, the image acquisition module 1522 or other image acquisition modules described herein. The objective lens and additional imaging optics can focus the scattered coherent light from the objective lens onto the imaging sensor. The objective lens and imaging optics can adjust magnification of the scattered coherent light to set an appropriate relationship between a speckles size of the scattered coherent light and a pixel size of the imaging sensor. The imaging sensor can digitize individual image frames and transfer them to one or more processors for processing.

In some implementations, the method 1300 can include one or more polarization steps to further reject light reflected from one or more of the internal optics, eye optics, or the retina. For example, the method 1300 can include passing the beam of coherent light through a first polarizer configured to pass light having a first polarization state, and passing the beam of scattered coherent light through a second polarizer configured to pass light having a second polarization state different from the first polarization state. The light passing through the first polarizer will have a first polarization state. Any light reflected by surfaces of the OID optics, surfaces of the eye optics, or the back of the retina, will retain this polarized state. The second polarizer can be offset from the polarized state of the reflected light, thereby blocking it. Light scattered by the retina, however, will have random polarization, and thus at least some of the scattered coherent light will pass through the second polarizer and on to the imaging sensor. In some implementations, the first and second polarizers can be discrete components. In some implementations, one or more of the polarizers can be integrated with one or more of the other optics of the OID; for example, one or more of the beam splitting elements may be a polarizing beam splitter.

In some implementations, the method 1300 can include transforming, using the objective lens, the scattered coherent light such that it comes into focus at a first image plane located along an optical path between the objective lens and the imaging sensor. The method 1300 can further include transforming, using a converging lens, the coherent light such that the coherent light defocuses into a second substantially uniform cross section at the first image plane.

In some implementations, the method 1300 can include generating an internal gaze fixation target light, combining the target light with the coherent light such that both the coherent light and the target light come into focus at the second image plane.

In some implementations, the method 1300 can include generating incoherent light, blocking a portion of the incoherent light using a light-blocking obstacle arranged in a center of an optical axis of the incoherent light, and transmitting the incoherent light to the eye such that an image of the light-blocking obstacle focuses into a dark disk at or near a point where the optical axis intersects the cornea.

In some implementations, the method 1300 can include receiving, at a processor from the image sensor, first data representing a first image taken with the coherent light; receiving, from the image sensor, second data representing a second image taken with the incoherent light; and processing the first data and the second data to generate a compound image. Such a process can be used, for example, to superimpose an LSCI image over a reflectance image of anatomy of the fundus.

Example Implementations of Systems, and Methods in Accordance with the Present Disclosure The following paragraphs (S1) through (S8) describe examples of systems and devices that may be implemented in accordance with the present disclosure.

(S1) A system may comprise an ophthalmic imaging device, including: a first light source configured to emit coherent light; an axicon lens configured to receive the coherent light from the first light source; a first beam splitting element configured to receive the coherent light from the axicon lens from a first direction and transmit the coherent light in a second direction; an objective lens configured to receive the coherent light from the beam splitting element, the axicon lens and the objective lens configured to transform the coherent light such that the coherent light focuses into an annular cross section at or near a cornea of an eye before defocusing into a substantially uniform cross section at or near a fundus of the eye; the objective lens further configured to receive scattered coherent light from the fundus; the first beam splitting element further configured to receive the scattered coherent light from the objective lens from the second direction and transmit it in a third direction; and an imaging sensor configured to receive scattered coherent light from the beam splitting element.

(S2) A system may be configured as described in paragraph (S1), and further include a first polarizer positioned along a first optical path between the axicon lens and the first beam splitting element, the first polarizer configured to pass light having a first polarization state; and a second polarizer positioned along a second optical path between the first beam splitting element and the image sensor, the second polarizer configured to pass light having a second polarization state different from the first polarization state.

(S3) A system may be configured as described in paragraph (S1) or paragraph (S2), and further include an aperture positioned along an optical path between the first beam splitting element and the image sensor, the aperture configured to act as a dominant aperture stop of an optical path between the fundus and the image sensor.

(S4) A system may be configured as described in any of paragraphs (S1) through (S3), wherein the objective lens is configured to transform the scattered coherent light such that it comes into focus at a first image plane located along an optical path between the objective lens and the first beam splitting element, and further includes: a converging lens located along an optical path of the coherent light between the axicon lens and the objective lens, the converging lens configured to transform the coherent light such that the coherent light defocuses into a second substantially uniform cross section at the first image plane.

(S5) A system may be configured as described in any of paragraphs (S1) through (S4), further include: a gaze fixation target configured to emit target light; and a second beam splitting element configured to receive the target light from a fourth direction and the coherent light from a fifth direction, and transmit the target light and the coherent light in a sixth direction towards the first beam splitting element.

(S6) A system may be configured as described in any of paragraphs (S1) through (S5), further include: a second light source configured to emit incoherent light; an optical element configured to create a dark region in a center of a beam of the incoherent light; and a second beam splitting element configured to receive the beam of incoherent light from a fourth direction and the coherent light from a fifth direction, and transmit the beam of incoherent light and the coherent light in a sixth direction towards the first beam splitting element.

(S7) A system may be configured as described in paragraph (S6), wherein the optical element is an obstacle configured to block a portion of the beam of incoherent light at a center of an optical axis of the beam of incoherent light.

(S8) A system may be configured as described in paragraph (S6) or paragraph (S7), and further include a processor configured to: receive, from the image sensor, first data representing a first set of one or more images taken with illumination from the coherent light source; receive, from the image sensor, second data representing a second set of one or more images taken with illumination from the incoherent light source; and process the first data and the second data to generate a compound image.

The following paragraphs (M1) through (M8) describe examples of methods that may be implemented in accordance with the present disclosure.

(M1) A system may perform a method that involves: generating a beam of coherent light; transforming the beam of coherent light using an axicon lens such that it focuses into a first substantially annular shape; transforming the beam of coherent light using an objective lens such that it focuses into a second substantially annular shape at or near a cornea of an eye before defocusing into a substantially uniform cross section at or near a fundus of the eye; receiving scattered coherent light from the fundus using the objective lens; and focusing the scattered coherent light from the objective lens onto an imaging sensor.

(M2) A system may perform the method described in paragraph (M1), further including: passing the beam of coherent light through a first polarizer configured to pass light having a first polarization state; and passing the beam of scattered coherent light through a second polarizer configured to pass light having a second polarization state different from the first polarization state.

(M3) A system may perform the method described in paragraph (M1) or paragraph (M2), further including passing the scattered coherent light through an aperture configured to act as a dominant aperture stop of an optical path between the fundus and the image sensor.

(M4) A system may perform the method described in any of paragraphs (M1) through (M3), further including: transforming, using the objective lens, the scattered coherent light such that it comes into focus at a first image plane located along an optical path between the objective lens and the imaging sensor; and transforming, using a converging lens, the coherent light such that the coherent light defocuses into a second substantially uniform cross section at the first image plane.

(M5) A system may perform the method described in paragraph (M4), further including: generating a gaze fixation target; and transforming, using a second converging lens, the light from the gaze fixation target such that the gaze fixation target come into focus at the first image plane.

(M6) A system may perform the method described in any of paragraphs (M1) through (M5), further including: generating incoherent light; creating a dark region at a center of an optical axis of a beam of the incoherent light; and transmitting the incoherent light to the eye such that beam of incoherent light comes into focus with a dark disk at or near a point where the optical axis intersects the cornea.

(M7) A system may perform the method described in paragraph (M6), further including blocking a center portion of the beam of incoherent light with an obstacle.

(M8) A system may perform the method described in paragraph (M6), further including: receiving, at a processor from the image sensor, first data representing a first image taken with the coherent light; receiving, from the image sensor, second data representing a second image taken with the incoherent light; and processing the first data and the second data to generate a compound image.

The following paragraphs (S1) through (S7) describe examples of systems and devices that may be implemented in accordance with the present disclosure.

(S1) A system may comprise an ophthalmic imaging device including: a first light source configured to emit at least two beams of coherent light; first and second cylindrical lenses configured to receive the two beams of coherent light, respectively, from the first light source; a first beam splitting element configured to receive the two beams of coherent light from the cylindrical lenses from a first direction and transmit the two beams of coherent light in a second direction; an objective lens configured to receive the two beams of coherent light from the beam splitting element, the cylindrical lenses and the objective lens configured to transform the two beams of coherent light such that the coherent light focuses into two rectangular shapes at or near a cornea of an eye before defocusing into a substantially uniform cross section at or near a fundus of the eye; the objective lens further configured to receive scattered coherent light from the fundus; the first beam splitting element further configured to receive the scattered coherent light from the objective lens from the second direction and transmit it in a third direction; and an imaging sensor configured to receive scattered coherent light from the beam splitting element.

(S2) A system may be configured as described in paragraph (S1), and further include: a first polarizer positioned along a first optical path between the cylindrical lenses and the first beam splitting element, the first polarizer configured to pass light having a first polarization state; and a second polarizer positioned along a second optical path between the first beam splitting element and the image sensor, the second polarizer configured to pass light having a second polarization state different from the first polarization state.

(S3) A system may be configured as described in paragraph (S1) or paragraph (S2), and further include an aperture positioned along an optical path between the first beam splitting element and the image sensor, the aperture configured to act as a dominant aperture stop of an optical path between the fundus and the image sensor.

(S4) A system may be configured as described in any of paragraphs (S1) through (S3), wherein the objective lens is configured to transform the scattered coherent light such that it comes into focus at a first image plane located along an optical path between the objective lens and the first beam splitting element, and further include: a converging lens located along an optical path of the coherent light between the cylindrical lenses and the objective lens, the converging lens configured to transform the two beams of coherent light such that the two beams of coherent light defocus into a second substantially uniform cross section at the first image plane.

(S5) A system may be configured as described in any of paragraphs (S1) through (S4), and further include: a gaze fixation target configured to emit target light; and a second beam splitting element configured to receive the target light from a fourth direction and the coherent light from a fifth direction, and transmit the target light and the coherent light in a sixth direction towards the first beam splitting element.

(S6) A system may be configured as described in any of paragraphs (S1) through (S5), and further include: a second light source configured to emit incoherent light; an optical element configured to create a dark region in a center of a beam of the incoherent light; and a second beam splitting element configured to receive the beam of incoherent light from a fourth direction and the coherent light from a fifth direction, and transmit the beam incoherent light and the coherent light in a sixth direction towards the first beam splitting element.

(S7) A system may be configured as described in paragraph (S6), wherein the optical element is an obstacle configured to block a portion of the beam of incoherent light at a center of an optical axis of the beam of incoherent light.

Various aspects and components of the embodiments of the OIDs and OID systems described herein, including OIDs 100, 1400, 1500, 300, 400, 600, and 1200 are not mutually exclusive and can be arranged in combinations that allow for different modalities of imaging. For example and without limitation, an OID according to the foregoing description can include one or both of coherent and incoherent light sources, and may or may not include a target image generator. In some embodiments, an OID system including a processor can receive images taken using different modalities and process them to generate a compound image. In some implementations, the processor can register the respective images to recognize and match features and overlay them. A display of the system can display the compound image to a user.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "back" and the like as used in this disclosure should be understood as referring to an arbitrary frame of reference, rather than to the ordinary gravitational frame of reference. Thus, a top surface, a bottom surface, a front surface, and a back surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

As used herein, the term "real time" shall be understood to mean the instantaneous moment of an event or condition, or the instantaneous moment of an event or condition plus short period of elapsed time used to make relevant measurements, optional computations, etc., and communicate the measurement, computation, or etc., wherein the state of an event or condition being measured is substantially the same as that of the instantaneous moment irrespective of the elapsed time interval. Used in this context "substantially the same" shall be understood to mean that the data for the event or condition remains useful for the purpose for which it is being gathered after the elapsed time period.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. An ophthalmic imaging device, comprising:
a first light source configured to emit coherent light;
an axicon lens configured to receive the coherent light from the first light source;
a first beam splitting element configured to receive the coherent light from the axicon lens from a first direction and transmit the coherent light in a second direction;
an objective lens configured to receive the coherent light from the first beam splitting element, the axicon lens and the objective lens configured to transform the coherent light such that the coherent light focuses into an annular cross section at or near a cornea of an eye before defocusing into a substantially uniform cross section at or near a fundus of the eye;
the objective lens further configured to receive scattered coherent light from the fundus;
the first beam splitting element further configured to receive the scattered coherent light from the objective lens from the second direction and transmit it in a third direction; and
an image sensor configured to receive scattered coherent light from the first beam splitting element.

2. The ophthalmic imaging device of claim 1, further comprising:
a first polarizer positioned along a first optical path between the axicon lens and the first beam splitting element, the first polarizer configured to pass light having a first polarization state; and
a second polarizer positioned along a second optical path between the first beam splitting element and the image sensor, the second polarizer configured to pass light having a second polarization state different from the first polarization state.

3. The ophthalmic imaging device of claim 1, further comprising:

an aperture positioned along an optical path between the first beam splitting element and the image sensor, the aperture configured to act as a dominant aperture stop of an optical path between the fundus and the image sensor.

4. The ophthalmic imaging device of claim 1, wherein the objective lens is configured to transform the scattered coherent light such that it comes into focus at a first image plane located along an optical path between the objective lens and the first beam splitting element, the ophthalmic imaging device further comprising:

a converging lens located along an optical path of the coherent light between the axicon lens and the objective lens, the converging lens configured to transform the coherent light such that the coherent light defocuses into a second substantially uniform cross section at the first image plane.

5. The ophthalmic imaging device of claim 1, further comprising:

a gaze fixation target configured to emit target light; and a second beam splitting element configured to receive the target light from a fourth direction and the coherent light from a fifth direction, and transmit the target light and the coherent light in a sixth direction towards the first beam splitting element.

6. The ophthalmic imaging device of claim 1, further comprising:

a second light source configured to emit incoherent light;

an optical element configured to create a dark region in a center of a beam of the incoherent light; and a second beam splitting element configured to receive the beam of incoherent light from a fourth direction and the coherent light from a fifth direction, and transmit the beam of incoherent light and the coherent light in a sixth direction towards the first beam splitting element.

7. The ophthalmic imaging device of claim 6, wherein the optical element is an obstacle configured to block a portion of the beam of incoherent light at a center of an optical axis of the beam of incoherent light.

8. The ophthalmic imaging device of claim 6, further comprising:

a processor configured to:

receive, from the image sensor, first data representing a first set of one or more images taken with illumination from the first light source;

receive, from the image sensor, second data representing a second set of one or more images taken with illumination from the second light source; and process the first data and the second data to generate a compound image.

9. A method comprising:

generating a beam of coherent light;

transforming the beam of coherent light using an axicon lens such that it focuses into a first substantially annular shape;

transforming the beam of coherent light using an objective lens such that it focuses into a second substantially annular shape at or near a cornea of an eye before defocusing into a substantially uniform cross section at or near a fundus of the eye;

receiving scattered coherent light from the fundus using the objective lens; and focusing the scattered coherent light from the objective lens onto an image sensor.

10. The method of claim 9, further comprising:

passing the beam of coherent light through a first polarizer configured to pass light having a first polarization state; and passing the beam of scattered coherent light through a second polarizer configured to pass light having a second polarization state different from the first polarization state.

11. The method of claim 9, further comprising:

passing the scattered coherent light through an aperture configured to act as a dominant aperture stop of an optical path between the fundus and the image sensor.

12. The method of claim 9, further comprising:

transforming, using the objective lens, the scattered coherent light such that it comes into focus at a first image plane located along an optical path between the objective lens and the image sensor; and transforming, using a converging lens, the coherent light such that the coherent light defocuses into a second substantially uniform cross section at the first image plane.

13. The method of claim 12, further comprising:

generating a gaze fixation target; and transforming, using a second converging lens, light from the gaze fixation target such that the gaze fixation target come into focus at the first image plane.

14. The method of claim 9, further comprising:

generating incoherent light;

creating a dark region at a center of an optical axis of a beam of the incoherent light; and transmitting the incoherent light to the eye such that beam of incoherent light comes into focus with a dark disk at or near a point where the optical axis intersects the cornea.

15. The method of claim 14, further comprising:

blocking a center portion of the beam of incoherent light with an obstacle.

16. The method of claim 14, further comprising:

receiving, at a processor from the image sensor, first data representing a first image taken with the coherent light;

receiving, from the image sensor, second data representing a second image taken with the incoherent light; and processing the first data and the second data to generate a compound image.

* * * * *